(12) United States Patent
Raycheck et al.

(10) Patent No.: US 11,938,004 B2
(45) Date of Patent: Mar. 26, 2024

(54) ABSORBENT ARTICLE HAVING A WAIST GASKETING ELEMENT

(71) Applicant: The Procter & Gamble Company, Cincinnati, OH (US)

(72) Inventors: Jeromy Thomas Raycheck, Cincinnati, OH (US); Thorsten Rinnert, Schwalbach Am Taunus (DE); Urmish Popatlal Dalal, Cincinnati, OH (US); Darren Lee Goad, Cold Spring, KY (US); Michael Brian Quade, Blue Ash, OH (US); Jason Edward Naylor, Loveland, OH (US); Uwe Schneider, Cincinnati, OH (US); Thomas F. Gross, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 282 days.

(21) Appl. No.: 16/864,292

(22) Filed: May 1, 2020

(65) Prior Publication Data

US 2020/0375815 A1 Dec. 3, 2020

Related U.S. Application Data

(60) Provisional application No. 62/930,808, filed on Nov. 5, 2019, provisional application No. 62/930,181, filed (Continued)

(51) Int. Cl.
*A61F 13/515* (2006.01)
*A61F 13/15* (2006.01)
(Continued)

(52) U.S. Cl.
CPC .. *A61F 13/15593* (2013.01); *A61F 13/15723* (2013.01); *A61F 13/15764* (2013.01); (Continued)

(58) Field of Classification Search
CPC .......... A61F 13/15593; A61F 13/15723; A61F 13/15764; A61F 13/49011; A61F 13/4906; (Continued)

(56) References Cited

U.S. PATENT DOCUMENTS 3,113,225 A 12/1963 Claus
3,562,041 A 2/1971 Robertson
(Continued)

FOREIGN PATENT DOCUMENTS

CN 1144472 A 3/1997
CN 1224606 A 8/1999
(Continued)

OTHER PUBLICATIONS

All Office Actions; U.S. Appl. No. 17/242,376, filed Apr. 28, 2021.
(Continued)

*Primary Examiner* — Susan S Su
(74) *Attorney, Agent, or Firm* — Charles R. Matson

(57) ABSTRACT

The present disclosure relates to absorbent articles having a waist gasketing element, with the gasketing element having an adhesive zone and one or more adhesive-free zones. At least a portion of the waist gasketing element is adhesively attached to a chassis of the absorbent article. Additionally, a portion of the waist gasketing element is mechanically attached to a portion of the absorbent article.

32 Claims, 8 Drawing Sheets

Related U.S. Application Data on Nov. 4, 2019, provisional application No. 62/930,198, filed on Nov. 4, 2019, provisional application No. 62/855,001, filed on May 31, 2019.

(51) Int. Cl.
  *A61F 13/49* (2006.01)
  *A61F 13/511* (2006.01)
  *A61F 13/58* (2006.01)
  *A61F 13/47* (2006.01)

(52) U.S. Cl.
  CPC .... *A61F 13/49011* (2013.01); *A61F 13/4906* (2013.01); *A61F 13/51113* (2013.01); *A61F 13/51121* (2013.01); *A61F 13/515* (2013.01); *A61F 13/58* (2013.01); *A61F 2013/15861* (2013.01); *A61F 2013/1591* (2013.01); *A61F 2013/4708* (2013.01); *A61F 2013/49092* (2013.01)

(58) Field of Classification Search
  CPC .......... A61F 13/51113; A61F 13/51121; A61F 13/515; A61F 13/58; A61F 2013/15861; A61F 2013/1591; A61F 2013/4708; A61F 2013/49092; A61F 13/49466; A61F 13/4758; A61F 13/49446; A61F 13/49453; A61F 13/4966; A61F 2013/4948
  See application file for complete search history.

(56) References Cited

U.S. PATENT DOCUMENTS

| | | |
|---|---|---|
| 3,733,238 A | 5/1973 | Long |
| 3,848,594 A | 11/1974 | Buell |
| 3,860,003 A | 1/1975 | Buell |
| 3,881,488 A | 5/1975 | Delanty et al. |
| 4,116,892 A | 9/1978 | Schwarz |
| 4,324,246 A | 4/1982 | Mullane et al. |
| 4,342,314 A | 8/1982 | Radel et al. |
| 4,463,045 A | 7/1984 | Ahr et al. |
| 4,515,595 A | 5/1985 | Kievit et al. |
| 4,556,146 A | 12/1985 | Swanson et al. |
| 4,568,344 A | 2/1986 | Suzuki et al. |
| 4,589,876 A | 5/1986 | Van Tilburg |
| 4,610,678 A | 9/1986 | Weisman et al. |
| 4,662,875 A | 5/1987 | Hirotsu |
| 4,673,402 A | 6/1987 | Weisman |
| 4,687,478 A | 8/1987 | Van Tillburg |
| 4,695,278 A | 9/1987 | Lawson |
| 4,704,115 A | 11/1987 | Buell |
| 4,795,454 A | 1/1989 | Dragoo |
| 4,795,510 A | 1/1989 | Wittrock et al. |
| 4,824,498 A | 4/1989 | Goodwin et al. |
| 4,834,735 A | 5/1989 | Alemany |
| 4,834,741 A | 5/1989 | Sabee |
| 4,846,815 A | 7/1989 | Scripps |
| 4,854,984 A | 8/1989 | Ball |
| 4,888,231 A | 12/1989 | Angstadt |
| 4,894,060 A | 1/1990 | Nestegard |
| 4,909,803 A | 3/1990 | Aziz |
| 4,940,464 A | 7/1990 | Van Gompel et al. |
| 4,946,527 A | 8/1990 | Battrell |
| 4,950,264 A | 8/1990 | Osborn, III |
| 5,009,653 A | 4/1991 | Osborn, III |
| 5,026,364 A | 6/1991 | Robertson |
| 5,092,861 A | 3/1992 | Nomura |
| 5,110,403 A | 5/1992 | Ehlert |
| 5,143,679 A | 9/1992 | Weber |
| 5,151,092 A | 9/1992 | Buell |
| 5,156,793 A | 10/1992 | Buell et al. |
| 5,167,897 A | 12/1992 | Weber et al. |
| 5,192,606 A | 3/1993 | Proxmire |
| 5,221,274 A | 6/1993 | Buell |
| 5,242,436 A | 9/1993 | Weil |
| 5,246,433 A | 9/1993 | Hasse |
| 5,267,992 A | 12/1993 | Van Tilburg |
| 5,308,345 A | 5/1994 | Herrin |
| 5,360,420 A | 11/1994 | Cook et al. |
| 5,407,507 A | 4/1995 | Ball |
| 5,422,172 A | 6/1995 | Wu |
| 5,518,801 A | 5/1996 | Chappell et al. |
| 5,540,796 A | 7/1996 | Fries |
| 5,562,646 A | 10/1996 | Goldman et al. |
| 5,569,234 A | 10/1996 | Buell |
| 5,571,096 A | 11/1996 | Dobrin |
| 5,575,783 A | 11/1996 | Clear |
| 5,599,335 A | 2/1997 | Goldman et al. |
| 5,628,097 A | 5/1997 | Benson et al. |
| 5,643,588 A | 7/1997 | Roe et al. |
| 5,669,894 A | 9/1997 | Goldman et al. |
| 5,674,216 A | 10/1997 | Buell et al. |
| 5,693,037 A | 12/1997 | Lee et al. |
| 5,700,255 A | 12/1997 | Curro |
| 5,702,551 A | 12/1997 | Huber et al. |
| 5,735,840 A | 4/1998 | Kline |
| 5,827,259 A | 10/1998 | Laux |
| 5,897,545 A | 4/1999 | Kline |
| 5,904,675 A | 5/1999 | Laux |
| 5,916,661 A | 6/1999 | Benson et al. |
| 5,928,212 A | 7/1999 | Kline |
| 5,957,908 A | 9/1999 | Kline |
| 5,961,997 A | 10/1999 | Swinehart |
| 5,968,025 A | 10/1999 | Roe et al. |
| 5,993,433 A | 11/1999 | St. Louis |
| 6,004,893 A | 12/1999 | Van Tilburg |
| 6,010,491 A | 1/2000 | Roe et al. |
| 6,036,796 A | 3/2000 | Halbert |
| 6,051,094 A | 4/2000 | Melbye et al. |
| 6,107,537 A | 8/2000 | Elder et al. |
| 6,107,539 A | 8/2000 | Palumbo et al. |
| 6,118,041 A | 9/2000 | Roe et al. |
| 6,120,487 A | 9/2000 | Ashton |
| 6,120,489 A | 9/2000 | Johnson |
| 6,149,934 A | 11/2000 | Krzysik et al. |
| 6,153,209 A | 11/2000 | Vega et al. |
| 6,156,023 A | 12/2000 | Yoshioka |
| 6,238,683 B1 | 5/2001 | Burnett et al. |
| 6,248,097 B1 | 6/2001 | Beitz et al. |
| 6,248,195 B1 | 6/2001 | Schmitz |
| 6,251,097 B1 | 6/2001 | Kline |
| 6,369,290 B1 | 4/2002 | Glaug |
| 6,409,883 B1 | 6/2002 | Makolin |
| 6,410,129 B2 | 6/2002 | Zhang et al. |
| 6,426,444 B2 | 7/2002 | Roe et al. |
| 6,432,098 B1 | 8/2002 | Kline et al. |
| 6,454,095 B1 | 9/2002 | Brisebois |
| 6,506,185 B1 | 1/2003 | Sauer et al. |
| 6,508,641 B1 | 1/2003 | Kubik |
| 6,545,197 B1 | 4/2003 | Mueller et al. |
| 6,568,530 B2 | 5/2003 | Takahashi |
| 6,572,595 B1 | 6/2003 | Klemp |
| 6,586,652 B1 | 7/2003 | Roe et al. |
| 6,601,705 B2 | 8/2003 | Molina |
| 6,617,016 B2 | 9/2003 | Zhang et al. |
| 6,627,787 B1 | 9/2003 | Roe et al. |
| 6,645,330 B2 | 11/2003 | Pargass |
| 6,648,864 B2 | 11/2003 | Ronn |
| 6,669,618 B2 | 12/2003 | Reising |
| 6,699,228 B1 | 3/2004 | Chmielewski et al. |
| 6,790,798 B1 | 9/2004 | Suzuki et al. |
| 6,825,393 B2 | 11/2004 | Roe et al. |
| 6,830,800 B2 | 12/2004 | Curro |
| 6,861,571 B1 | 3/2005 | Roe et al. |
| 7,087,287 B2 | 8/2006 | Curro |
| 7,371,302 B2 | 5/2008 | Miyamoto et al. |
| 7,569,039 B2 | 8/2009 | Matsuda et al. |
| 7,785,309 B2 | 8/2010 | Van Gompel et al. |
| 7,803,244 B2 | 9/2010 | Siqueira |
| 7,824,594 B2 | 11/2010 | Qureshi |
| 7,896,641 B2 | 3/2011 | Qureshi |
| 8,062,572 B2 | 11/2011 | Qureshi |

(56) References Cited

U.S. PATENT DOCUMENTS

| | | |
|---|---|---|
| 8,118,801 B2 | 2/2012 | Macura |
| 8,186,296 B2 | 5/2012 | Brown et al. |
| 8,257,333 B2 | 9/2012 | Hancock-cooke et al. |
| 8,395,012 B2 | 3/2013 | Bacon et al. |
| 8,496,638 B2 | 7/2013 | Lord et al. |
| 8,608,720 B2 | 12/2013 | Erickson et al. |
| 8,715,464 B2 | 5/2014 | Young et al. |
| 8,778,127 B2 | 7/2014 | Schneider et al. |
| 8,936,697 B2 | 1/2015 | Scharpf et al. |
| 8,956,493 B2 | 2/2015 | Tenorio et al. |
| 9,005,392 B2 | 4/2015 | Schneider et al. |
| 9,248,054 B2 | 2/2016 | Brown et al. |
| 9,265,672 B2 | 2/2016 | Brown et al. |
| 9,283,124 B2 | 3/2016 | Hashimoto et al. |
| 9,295,590 B2 | 3/2016 | Brown et al. |
| 9,468,569 B2 | 10/2016 | Hancock-cooke et al. |
| 9,687,580 B2 | 6/2017 | Schonbeck |
| 9,913,871 B2 | 3/2018 | Ellington et al. |
| 9,962,297 B2 | 5/2018 | Eckstein |
| 10,052,237 B2 | 8/2018 | Galie |
| 10,159,610 B2 | 12/2018 | Barnes |
| 10,470,943 B2 | 11/2019 | Jang |
| 11,096,836 B2 | 8/2021 | Bishop et al. |
| 11,369,526 B2 | 6/2022 | Matsui et al. |
| 11,554,055 B2 | 1/2023 | Bishop et al. |
| 2002/0064639 A1 | 5/2002 | Rearick et al. |
| 2002/0165170 A1 | 11/2002 | Wilson et al. |
| 2003/0121380 A1 | 7/2003 | Cowell |
| 2003/0154904 A1 | 8/2003 | Klofta et al. |
| 2003/0187414 A1 | 10/2003 | Reiss et al. |
| 2003/0233082 A1 | 12/2003 | Kline |
| 2004/0097895 A1 | 5/2004 | Busam et al. |
| 2004/0122413 A1 | 6/2004 | Roessler |
| 2004/0158212 A1 | 8/2004 | Ponomarenko et al. |
| 2004/0196734 A1 | 10/2004 | Mehta et al. |
| 2005/0096616 A1 | 5/2005 | Arora et al. |
| 2005/0107764 A1 | 5/2005 | Matsuda et al. |
| 2005/0171498 A1 | 8/2005 | Reiss et al. |
| 2005/0217812 A1 | 10/2005 | Stoyanov et al. |
| 2006/0094320 A1 | 5/2006 | Chen et al. |
| 2006/0129115 A1 | 6/2006 | Visscher |
| 2006/0167434 A1 | 7/2006 | Ashton et al. |
| 2006/0196796 A1 | 9/2006 | Motsch et al. |
| 2006/0264862 A1 | 11/2006 | Yoshida et al. |
| 2006/0264863 A1 | 11/2006 | Blyth |
| 2006/0287637 A1* | 12/2006 | Lam ............... A61F 13/49015 604/389 |
| 2007/0032772 A1 | 2/2007 | Ehrnsperger |
| 2007/0078427 A1 | 4/2007 | Raycheck |
| 2007/0093769 A1 | 4/2007 | Kline |
| 2007/0149937 A1 | 6/2007 | Reiss et al. |
| 2007/0219521 A1 | 9/2007 | Hird |
| 2007/0287980 A1 | 12/2007 | Kline et al. |
| 2008/0099360 A1 | 5/2008 | Smith |
| 2008/0250681 A1 | 10/2008 | Jackson |
| 2008/0269704 A1 | 10/2008 | Hansson et al. |
| 2009/0149827 A1 | 6/2009 | Mlinar et al. |
| 2009/0155325 A1 | 6/2009 | Magin et al. |
| 2009/0157034 A1 | 6/2009 | Mattingly et al. |
| 2009/0204090 A1 | 8/2009 | Dennis et al. |
| 2009/0294044 A1 | 12/2009 | Gill et al. |
| 2009/0312730 A1 | 12/2009 | LaVon et al. |
| 2010/0181223 A1 | 7/2010 | Warren |
| 2010/0221496 A1 | 9/2010 | De Jong |
| 2010/0230857 A1 | 9/2010 | Muhs et al. |
| 2010/0305532 A1 | 12/2010 | Ashton et al. |
| 2011/0040273 A1 | 2/2011 | Sablone |
| 2011/0046594 A1 | 2/2011 | Sablone |
| 2011/0073513 A1 | 3/2011 | Weisman et al. |
| 2011/0139657 A1 | 6/2011 | Hird |
| 2011/0139658 A1 | 6/2011 | Hird |
| 2011/0139659 A1 | 6/2011 | Hird |
| 2011/0139662 A1 | 6/2011 | Hird |
| 2011/0152812 A1 | 6/2011 | Hird |
| 2011/0215017 A1 | 9/2011 | Coulter et al. |
| 2011/0315585 A1 | 12/2011 | Meyer et al. |
| 2011/0319849 A1 | 12/2011 | Collias et al. |
| 2012/0061015 A1 | 3/2012 | LeVon et al. |
| 2012/0061016 A1 | 3/2012 | LeVon et al. |
| 2012/0143165 A1 | 6/2012 | Macura |
| 2012/0206265 A1 | 8/2012 | Solazzo et al. |
| 2012/0276341 A1 | 11/2012 | Lake |
| 2012/0277703 A1 | 11/2012 | Rhein |
| 2012/0277713 A1 | 11/2012 | Raycheck |
| 2013/0018339 A1 | 1/2013 | Kaiser et al. |
| 2013/0072887 A1 | 3/2013 | LeVon et al. |
| 2013/0126071 A1 | 5/2013 | Shin et al. |
| 2013/0211356 A1 | 8/2013 | Nishikawa et al. |
| 2013/0255861 A1 | 10/2013 | Schneider |
| 2013/0255862 A1 | 10/2013 | Schneider et al. |
| 2013/0255863 A1 | 10/2013 | LaVon et al. |
| 2013/0255864 A1 | 10/2013 | Schneider et al. |
| 2013/0255865 A1 | 10/2013 | Brown et al. |
| 2013/0274697 A1 | 10/2013 | Godlewski |
| 2013/0306226 A1 | 11/2013 | Zink |
| 2013/0313149 A1 | 11/2013 | Hird et al. |
| 2014/0005621 A1 | 1/2014 | Roe |
| 2014/0039422 A1 | 2/2014 | Scott |
| 2014/0079919 A1 | 3/2014 | Bunnelle |
| 2014/0093697 A1 | 4/2014 | Perry et al. |
| 2014/0148773 A1 | 5/2014 | Brown |
| 2014/0272370 A1 | 9/2014 | Broyles |
| 2014/0276512 A1 | 9/2014 | Cheng et al. |
| 2014/0352090 A1 | 12/2014 | Schuchter |
| 2014/0371700 A1 | 12/2014 | Patel et al. |
| 2015/0283003 A1 | 10/2015 | Rosati |
| 2015/0366724 A1 | 12/2015 | Fukuzawa et al. |
| 2015/0374561 A1 | 12/2015 | Hubbard, Jr. et al. |
| 2016/0101003 A1 | 4/2016 | Jennewein et al. |
| 2016/0206774 A1 | 7/2016 | Hird |
| 2016/0270973 A1 | 9/2016 | Surushe et al. |
| 2016/0270979 A1 | 9/2016 | Raycheck et al. |
| 2016/0270980 A1 | 9/2016 | Raycheck et al. |
| 2016/0350828 A1 | 12/2016 | Schmidt et al. |
| 2017/0000658 A1* | 1/2017 | Chatterjee ............... A61F 13/49 |
| 2017/0056253 A1 | 3/2017 | Chester et al. |
| 2017/0246052 A1 | 8/2017 | Ludwig |
| 2017/0252229 A1 | 9/2017 | Bonelli |
| 2017/0290712 A1 | 10/2017 | Findley et al. |
| 2017/0296399 A1 | 10/2017 | Kline et al. |
| 2017/0313034 A1 | 11/2017 | Takeda et al. |
| 2017/0319399 A1 | 11/2017 | Desai et al. |
| 2017/0333261 A1 | 11/2017 | Chatterjee et al. |
| 2017/0333262 A1 | 11/2017 | Chatterjee et al. |
| 2018/0042777 A1 | 2/2018 | Dalal |
| 2018/0042778 A1 | 2/2018 | Lenser et al. |
| 2018/0042779 A1 | 2/2018 | Lenser et al. |
| 2018/0042780 A1 | 2/2018 | Sells |
| 2018/0042785 A1 | 2/2018 | Dalal |
| 2018/0042786 A1 | 2/2018 | Mueller et al. |
| 2018/0042787 A1 | 2/2018 | Lenser et al. |
| 2018/0055698 A1* | 3/2018 | Bishop ............... A61F 13/49466 |
| 2018/0140469 A1 | 5/2018 | Kane et al. |
| 2018/0169964 A1 | 6/2018 | Schneider |
| 2018/0250171 A1 | 9/2018 | Back et al. |
| 2018/0256419 A1 | 9/2018 | Mcgilloway et al. |
| 2018/0271716 A1 | 9/2018 | Dalal |
| 2018/0360739 A1 | 12/2018 | Lorenz et al. |
| 2018/0369091 A1 | 12/2018 | Avshalomov |
| 2019/0010258 A1 | 1/2019 | Mitchell et al. |
| 2019/0070042 A1 | 3/2019 | Beck |
| 2019/0083325 A1 | 3/2019 | Mccormick |
| 2019/0083331 A1 | 3/2019 | Barnes |
| 2019/0175417 A1 | 6/2019 | Graham |
| 2020/0038256 A1 | 2/2020 | Jang et al. |
| 2020/0054496 A1 | 2/2020 | Mccormick et al. |
| 2020/0054497 A1 | 2/2020 | Mccormick et al. |
| 2020/0078230 A1 | 3/2020 | Mccormick et al. |
| 2020/0093652 A1 | 3/2020 | Mccormick et al. |
| 2020/0093653 A1 | 3/2020 | Mccormick et al. |
| 2020/0121519 A1 | 4/2020 | Mccormick et al. |
| 2020/0155372 A1* | 5/2020 | Kleuskens ............... A61F 13/49466 |
| 2020/0163812 A1 | 5/2020 | Zuleger et al. |
| 2020/0197560 A1 | 6/2020 | Buchalter |

(56) References Cited

U.S. PATENT DOCUMENTS

| | | |
|---|---|---|
| 2020/0375807 A1 | 12/2020 | Schneider et al. |
| 2020/0375816 A1 | 12/2020 | Mccormick et al. |
| 2021/0346211 A1 | 11/2021 | Kilbacak et al. |
| 2021/0346213 A1 | 11/2021 | Kilbacak et al. |

FOREIGN PATENT DOCUMENTS

| | | | | |
|---|---|---|---|---|
| CN | 1328438 | A | 12/2001 | |
| CN | 101327156 | A | 12/2008 | |
| CN | 101389237 | A | 3/2009 | |
| CN | 104244881 | A | 12/2014 | |
| CN | 106038076 | A | 10/2016 | |
| CN | 106456410 | A | 2/2017 | |
| CN | 107405227 | A | 11/2017 | |
| CN | 107809989 | A | 3/2018 | |
| CN | 107820419 | A | 3/2018 | |
| CN | 108472171 | A * | 8/2018 | ............ A61F 13/49 |
| CN | 109069313 | A | 12/2018 | |
| CN | 109069315 | A | 12/2018 | |
| CN | 109843242 | A | 6/2019 | |
| CN | 114025727 | A | 2/2022 | |
| EP | 2260813 | B1 | 7/2015 | |
| JP | 2002232009 | A | 8/2002 | |
| JP | 2002541918 | A | 12/2002 | |
| JP | 2008074327 | A | 4/2008 | |
| JP | 2008113684 | A | 5/2008 | |
| JP | 2008113685 | A | 5/2008 | |
| JP | 2010269029 | A | 12/2010 | |
| JP | 2011062226 | A | 3/2011 | |
| JP | 2012243462 | A | 12/2012 | |
| JP | 2013164937 | A | 8/2013 | |
| JP | 2013168434 | A | 8/2013 | |
| JP | 2013180171 | A | 9/2013 | |
| JP | 2016112341 | A | 6/2016 | |
| JP | 2016182169 | A | 10/2016 | |
| JP | 2017060635 | A | 3/2017 | |
| RU | 24771 | U1 | 8/2002 | |
| WO | WO 95011650 | A1 | 5/1995 | |
| WO | 9524173 | A2 | 9/1995 | |
| WO | 2007106929 | A1 | 9/2007 | |
| WO | 2009012284 | A1 | 1/2009 | |
| WO | 2013002691 | A1 | 1/2013 | |
| WO | 2014103464 | A1 | 7/2014 | |
| WO | 2016023016 | A1 | 2/2016 | |
| WO | 2017118612 | A1 | 7/2017 | |
| WO | 2017124092 | A1 | 7/2017 | |
| WO | 2020004476 | A1 | 1/2020 | |
| WO | 2020004499 | A1 | 1/2020 | |
| WO | 2020115916 | A1 | 6/2020 | |
| WO | 2020116554 | A1 | 6/2020 | |
| WO | 2020116592 | A1 | 6/2020 | |
| WO | 2020116595 | A1 | 6/2020 | |
| WO | WO-2020115916 | A1 * | 6/2020 | ....... A61F 13/49413 |
| WO | WO-2020116593 | A1 * | 6/2020 | ........... A61F 13/475 |

OTHER PUBLICATIONS

PCT International Search Report, dated Jul. 30, 2020, 14 pages.
All Office Actions, U.S. Appl. No. 16/864,267.
All Office Actions, U.S. Appl. No. 16/885,622.
All Office Actions, U.S. Appl. No. 17/029,211.
All Office Actions, U.S. Appl. No. 17/029,486,
International Search Report and Written Opinion; Application Ser. No. PCT/US2020/030893; dated Jul. 27, 2020, 13 pages.
International Search Report and Written Opinion; Application Ser. No. PCT/US2020/070569; dated Dec. 4, 2020, 13 pages.
Unpublished U.S. Appl. No. 17/029,211, filed Sep. 23, 2020, to first inventor et. al.
Unpublished U.S. Appl. No. 17/029,486, filed Sep. 23, 2020, to first inventor et. al.
"Surround." Merriam-Webster.com Dictionary, Merriam-Webster, https ://www .merriam-webster.com/dictionary/surround. Accessed Jun. 15, 2021, 8 Pages.
Epsilon, Water Soluble Dyes/Solvent Green 7 and Corresponding Material Safety Data Sheet, Jul. 15, 2013, 5 pages.
All Office Actions; U.S. Appl. No. 18/126,534, filed Mar. 27, 2023.
Unpublished U.S. Appl. No. 18/126,534, filed Mar. 27, 2023, to Tanner Laurie Williams et al.
All Office Actions; U.S. Appl. No. 18/493,083, filed Oct. 24, 2023.
Unpublished U.S. Appl. No. 18/493,083, filed Oct. 24, 2023, to Jeromy Thomas Raycheck et al.

* cited by examiner

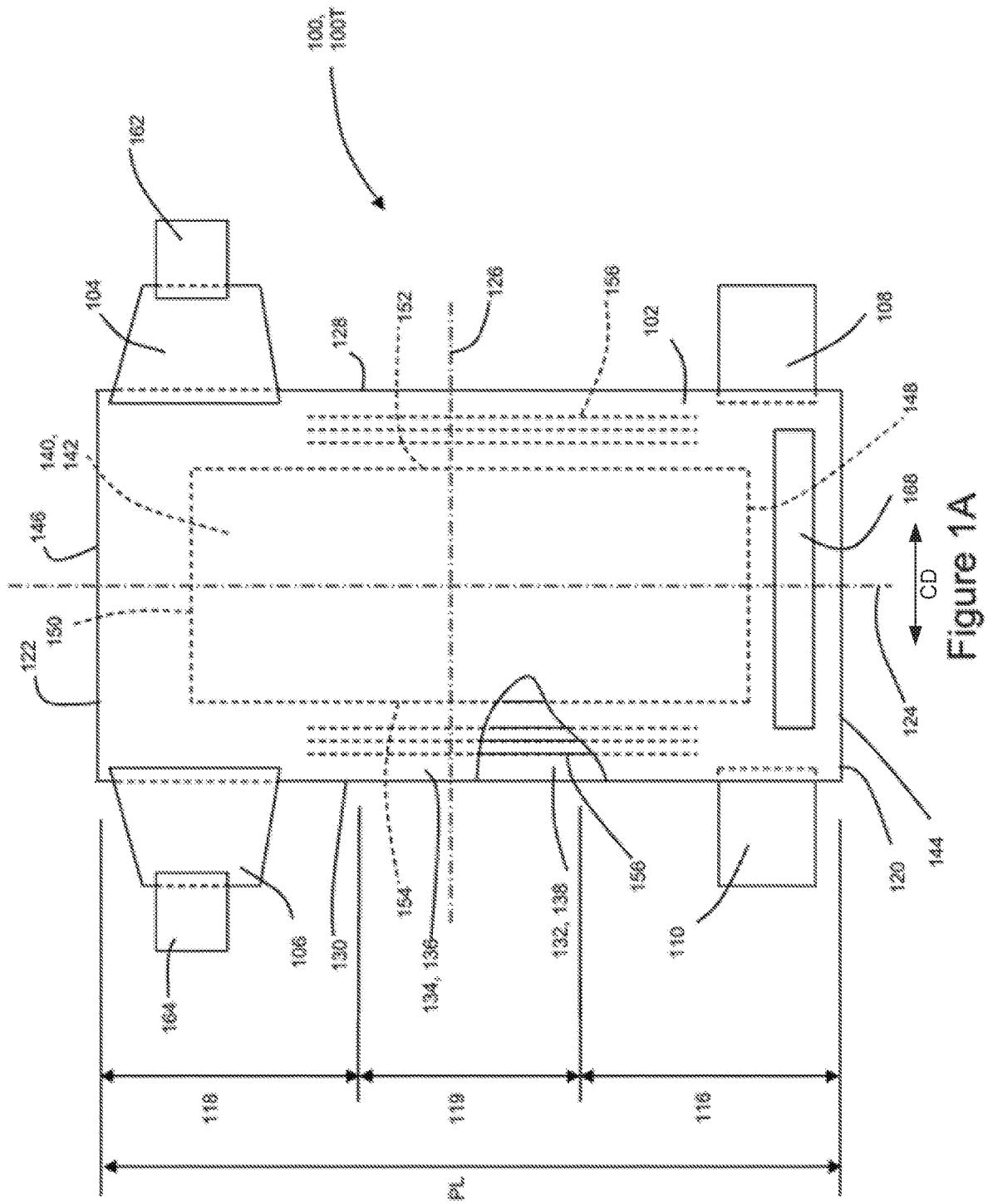

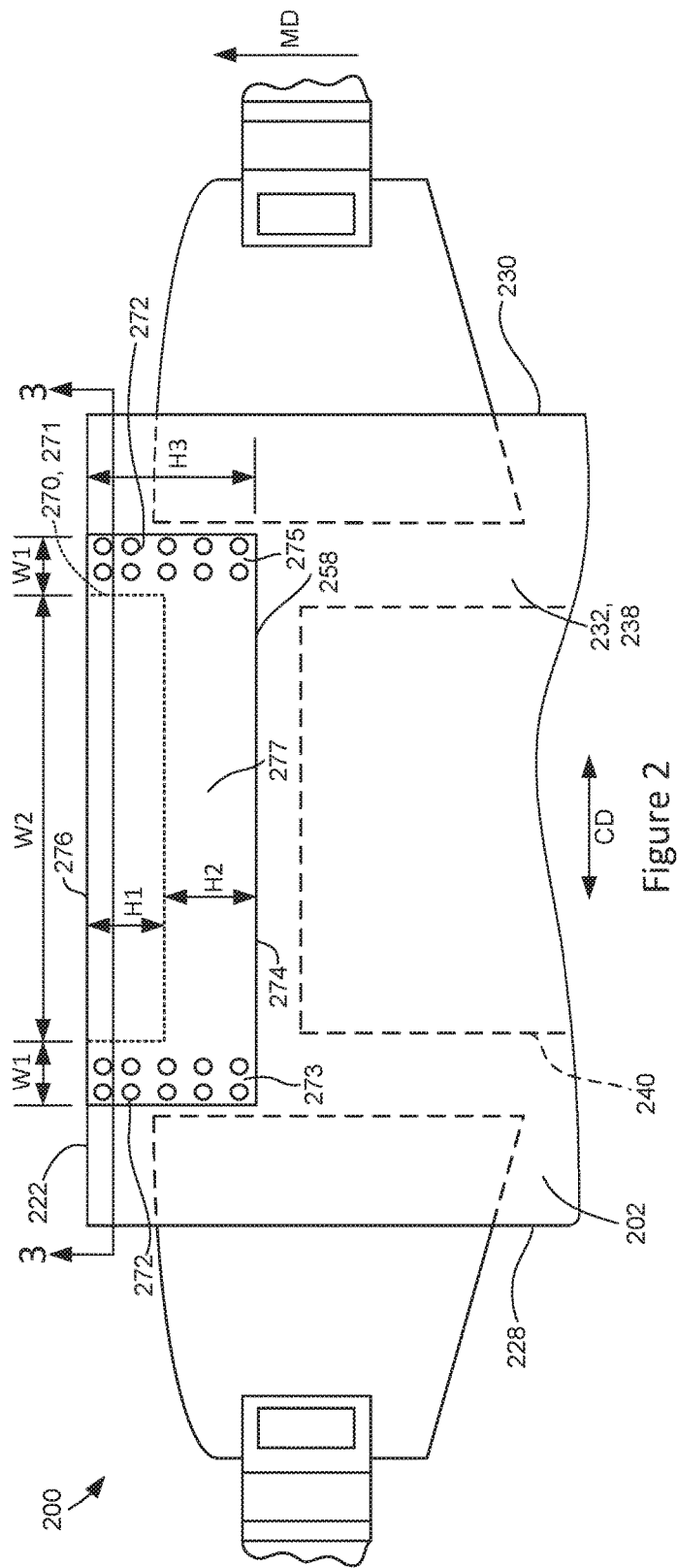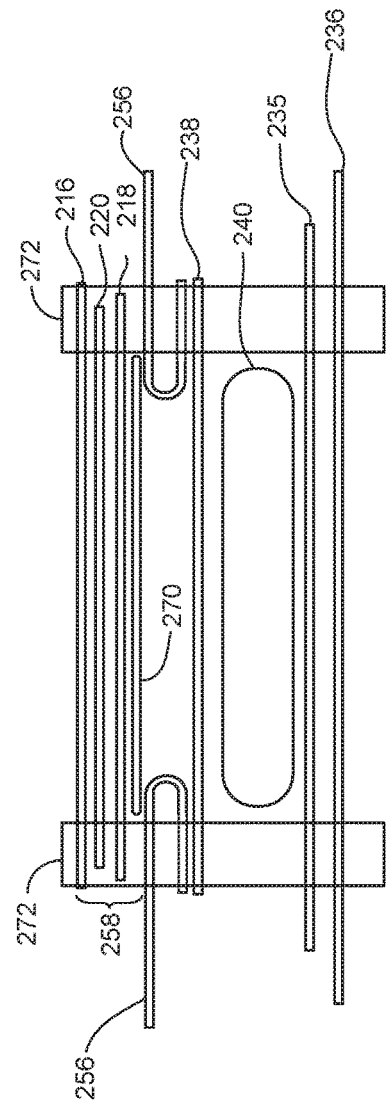

ABSORBENT ARTICLE HAVING A WAIST GASKETING ELEMENT

CROSS REFERENCE TO RELATED APPLICATION

This application claims the benefit of U.S. Provisional Patent Application Ser. No. 62/930,181, filed on Nov. 4, 2019; U.S. Provisional Patent Application No. 62/855,001, filed on May 31, 2019; U.S. Provisional Patent Application No. 62/930,198, filed on Nov. 4, 2019; and U.S. Provisional Patent Application No. 62/930,808, filed on Nov. 5, 2019, which are all hereby incorporated by reference herein.

FIELD OF THE INVENTION

The present disclosure relates to disposable absorbent articles having a waist gasketing element, and more specifically to waist gasketing elements having an adhesive free-zone and an adhesive zone.

BACKGROUND OF THE INVENTION

Various types of articles, such as for example, diapers and other absorbent articles, have components that include elastic parts, such as for example, waistbands. In some configurations, waistbands may be provided as a single layer of elastic material, such as an elastic film. In some configurations, the waistbands may be provided as an elastic laminate that may include elastic material bonded to one or more substrates such as nonwovens, wherein the elastic material may include an elastic film and/or elastic strands. Providing an elasticated waistband at the top edge of the disposable absorbent article can have improved fit and containment. An elasticated waistband can help contain exudates by providing increased pressure between the skin and the article to form a seal that helps to prevent exudates from exiting the product in the waist area. Additionally, elasticated waistbands can physically close gaps that may otherwise be formed when the wearer moves into positions, such as bending forward at the waist.

Waistbands can be located at one or both of the front and back edges of absorbent articles, and in closed form "pant" articles, they can be continuously formed to provide a waistband around the entire top edge of the article. In some articles, a waistband can be provided on the back only and spaced down from the edge of the article to close gaps in the rear part of the article. Articles providing a waistband that is spaced down from the edge typically exhibit larger ruffles at the top edge of the product as compared to articles having a waistband that is coterminous with the edge of the article. These ruffles can appear to caregivers as gaps from which exudates could leak even though the waist may close the gaps just below this region. Therefore, articles with waistbands that are coterminous with the edge of the article are may be preferred. However, some caregivers perceive waistbands that are spaced down from the edge of the article as being better leakage barriers.

Elasticated waistbands can comprise a variety of elastic materials such as stranded elastics, films, elastic nonwovens materials, elastic glues, and so forth. These materials can have a high coefficient of friction and/or can be tacky. Such elastic portions of the materials can be laminated to another material with a lower coefficient of friction, such as a polypropylene nonwoven, to protect the wearer from direct contact with the elastic material. The materials can be laminated together with a variety of means, including adhesively bonding, mechanically bonding, thermally bonding, or other suitable techniques. For some absorbent articles the material laminated with the elastic material is material already existing for another reason in an absorbent article, such as a topsheet, or for other absorbent articles it could be a material specifically designed to cover the elastic in the waistband region only. Therefore, with regard to waistbands that are externally attached to the inside surface (i.e., body-facing side) of the article, a material specifically designed to cover the elastic material can be used. Therefore, it can be beneficial to provide a waistband that is both covered with a material and provided at the longitudinal edges of the article.

Waistbands that are attached to the external, inside surface of the article can be attached using a variety of means, including mechanically attached, adhesively attached, thermally attached, co-formed, and so forth. The most typical way in the industry to attach a waistband to the external surface is adhesive bonding. Adhesive equipment applications typically cost less than comparable mechanical applications, are readily known in the industry, and perform well on most waistband applications, particularly for waistbands that are positioned on an internal surface of the diaper (i.e. sandwiched) by existing materials such as topsheet and or backsheet. Sandwiching the waistband ensures that any of the adhesive applied to attach the waistband is covered and is not in direct contact with the user.

With externally applied waistbands, however, problems can occur that are detrimental to the efficacy of the absorbent article and have not been resolved completely within high speed absorbent article manufacturing applications. Most predominantly, a portion of the adhesive can become exposed to the user surface of the article and stick to the user during use and removal of the product, or otherwise make it difficult for the product to be prepared for application to the user. The adhesive can become exposed through a variety of ways. For instance, variations in the waistband attachment can lead to the lateral edges (i.e., left and right side edges) folding over or rolling up thereby exposing the underside of the waistbands and the adhesive. Further, the adhesively attached waistbands can snag on various componentry of the equipment during subsequent manufacturing or stick to various processes. In addition, adhesives can take time to solidify in the manufacturing process. If there are other processes downstream of the waistband attachment process, there may not be sufficient time for the adhesive to solidify and thus, waistbands can be easily pulled off of the article in the process with a very low force. Additionally, many times the adhesive is applied to a layer of the article such as the topsheet, and variation related to attaching the waistband, particularly in high speed manufacturing processes, can lead to an edge of the adhesive becoming exposed on one side or the other.

An approach to address the issues created with adhesive bonding of externally applied waistbands is to mechanically attach them. A mechanical attachment process can bond the waistband to the article immediately so there is smaller risk that the waistband will fall off during subsequent processing. In addition, mechanical attachments are not tacky, so even if a portion of the waistband rolls up, it will not stick to the user. Nevertheless, mechanical attachment presents several other issues, particularly in the central absorbent region of an article—especially when waistbands are attached to the chassis after the absorbent core and the chassis have already been combined. For instance, mechanical attachment can create holes that can lead to leaks of bodily exudates through the outer cover of the absorbent article. Variations in the process or the equipment manufacture can also make it difficult to create adequate bonds. In addition, mechanical bonding over the absorbent core of the absorbent article can be ineffective if the mechanical bond contacts airfelt or absorbent gel material (AGM) that is distributed within the absorbent core. Airfelt is wood pulp based and does not melt and does not bond well to the rest of the polymers in the article, leading to poor bonding. AGM can burn and become dark when subjected to a mechanical bonding process and also does not chemically pair well with other polymers, such as polypropylene. As a result, poor bonding or no bonding can occur.

Therefore, it would be advantageous to have an externally applied waistband that addresses the problems associated with adhesively bonding at the edges, namely, exposed adhesive, and premature falling off in the process. It would also be advantageous to have an externally applied waistband that addresses the problems associated with mechanically bonding near the absorbent core, namely, holes in the outer cover and burnt spots. It would further be advantageous to have an externally applied waistband that is attached at or near the longitudinal edges of the article to prevent large gathers that may be perceived as gaps and that is laminated to a nonwoven material to protect the user from the high friction materials of the elastomer.

SUMMARY OF THE INVENTION

In one form, a disposable absorbent article comprises a front waist region, a back waist region, and a crotch region disposed between the first and second waist regions; a longitudinal axis and a lateral axis; a front waist edge, a back waist edge, a first side edge extending longitudinally and a second side edge extending longitudinally; and a chassis comprising a topsheet, a backsheet, and an absorbent core disposed between the topsheet and the backsheet. The disposable absorbent article also comprises a waist gasketing element comprising a proximal end edge, a distal end edge, a first side edge, and a second side edge, and an elastic material. The disposable absorbent article also comprises a leg gasketing element comprising a proximal end edge, a distal end edge, a first side edge, a second side edge, and an elastic material. At least a portion of the waist gasketing element is adhesively attached to the chassis and wherein at least a portion of the waist gasketing element is mechanically attached to the chassis, wherein the waist gasketing element comprises an adhesive zone, a first adhesive-free zone, and a second adhesive-free zone.

In another form a disposable absorbent article comprises a front waist region, a back waist region, and a crotch region disposed between the front and back waist regions; a longitudinal axis and a lateral axis; a front waist edge, a back waist edge, a first side edge extending longitudinally and a second side edge extending longitudinally; and a chassis comprising a topsheet, a backsheet, and an absorbent core disposed between the topsheet and the backsheet. The disposable absorbent article also comprises a waist gasketing element comprising a proximal end edge, a distal end edge, a first side edge and a second side edge, and an elastic material. The disposable absorbent article also comprises a leg gasketing element comprising a proximal end edge, a distal end edge, a first side edge and a second side edge, and an elastic material. At least a portion of the waist gasketing element is adhesively attached to the chassis and wherein at least a portion of the waist gasketing element is mechanically attached to the leg gasketing element, wherein the waist gasketing element comprises an adhesive zone, a first adhesive-free zone, and a second adhesive-free zone.

BRIEF DESCRIPTION OF THE DRAWINGS

FIG. 1A is a partially cut away plan view of an absorbent article in the form of a taped absorbent article that may include one or more waist gasketing elements in accordance with the present disclosure with the portion of the absorbent article that faces away from a wearer oriented towards the viewer.

FIG. 2 is a plan view of a back waist region of an absorbent article with the portion of the absorbent article that faces toward a wearer oriented towards the viewer.

FIG. 3 is a cross-sectional view of absorbent article taken along line 3-3 in FIG. 2.

DETAILED DESCRIPTION OF THE INVENTION

Figure 1B:
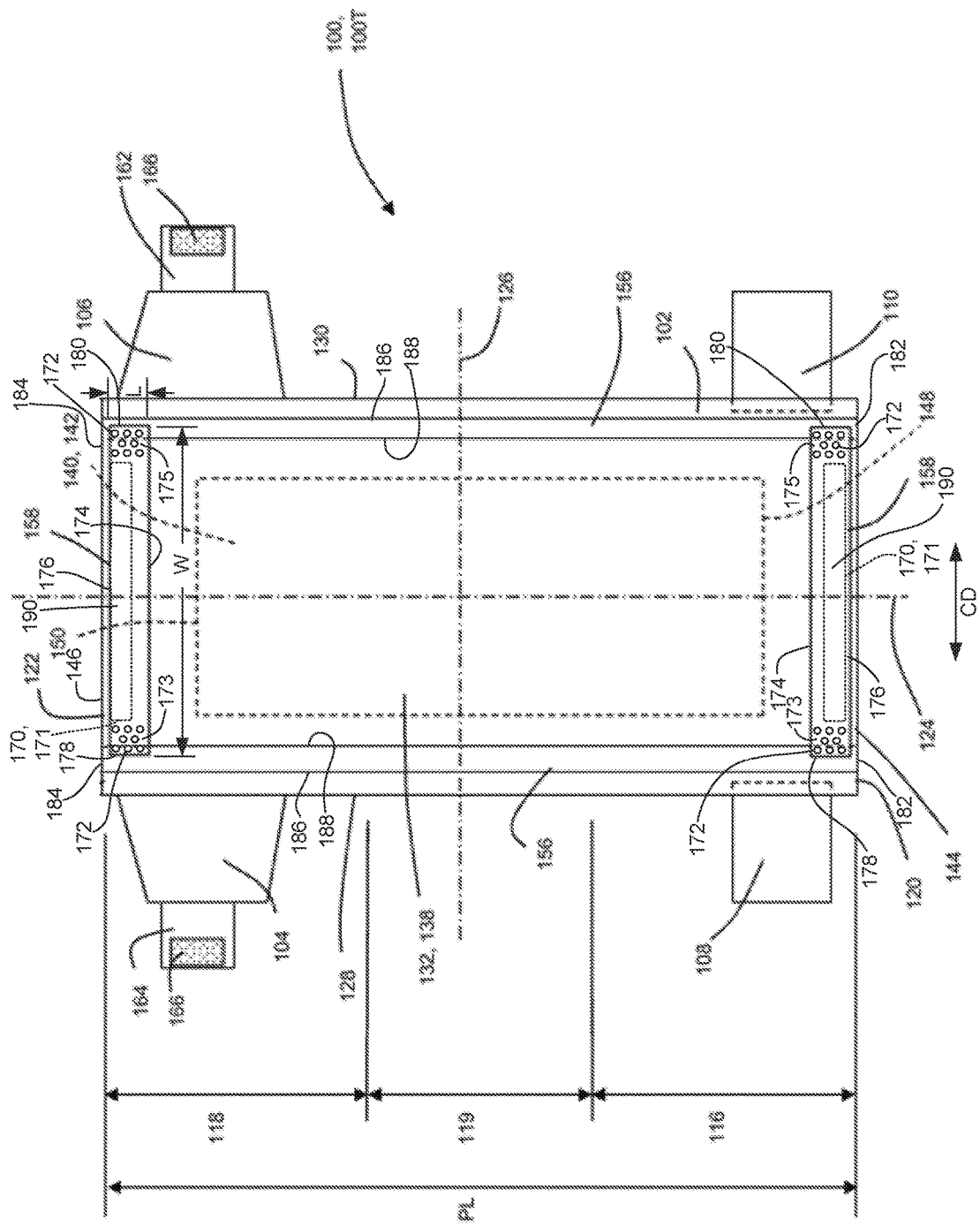
FIG. 1B is a plan view of the absorbent article of FIG. 1A that may include one or more waist gasketing elements in accordance with the present disclosure with the portion of the absorbent article that faces toward a wearer oriented towards the viewer.

The following term explanations may be useful in understanding the present disclosure:

"Absorbent article" is used herein to refer to consumer products whose primary function is to absorb and retain soils and wastes. Absorbent articles can comprise sanitary napkins, tampons, panty liners, interlabial devices, wound dressings, wipes, disposable diapers including taped diapers and diaper pants, inserts for diapers with a reusable outer cover, adult incontinent diapers, adult incontinent pads, and adult incontinent pants. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

The term "feminine hygiene articles" refers to disposable absorbent articles used by women for catamenial protection. Such feminine hygiene articles may include sanitary napkins, tampons, interlabial products, incontinence devices, and pantiliners. Non-limiting examples of panty liners and sanitary napkins include those disclosed in U.S. Pat. Nos. 4,324,246; 4,463,045; 4,342,314; 4,556,146; 4,589,876; 4,687,478; 4,950,264; 5,009,653; 5,267,992; and 6,004,893, which are all incorporated by reference herein.

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element and configurations whereby an element is indirectly secured to another element by affixing the element to intermediate member(s), which in turn are affixed to the other element.

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers of fibrous materials, nonwovens, and films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. In some configurations, a nonwoven may comprise a polyolefin based nonwoven, including but not limited to nonwovens having polypropylene fibers and/or polyethylene fibers and/or bicomponent fibers comprising a polyolefin and/or blends of fibers containing cotton or other organic materials. Nonlimiting examples of suitable fibers include spunbond, spunlaid, meltblown, spunmelt, solvent-spun, electrospun, carded, film fibrillated, melt-film fibrillated, air-laid, dry-laid, wet-laid staple fibers, hydroentangled, and other nonwoven web materials formed in part or in whole of polymer fibers as known in the art, and workable combinations thereof. Nonwovens do not have a woven or knitted filament pattern. It is to be appreciated that nonwovens having various basis weights can be used in accordance with the present disclosure. For example, some nonwovens may have a basis weight of at least about 8 gsm, 12 gsm, 16 gsm, 20 gsm, 25 gsm, 30 gsm, 40 gsm, or 65 gsm. Some nonwovens may have basis weights of about 8 gsm to about 65 gsm, specifically reciting all 1 gsm increments within the above-recited ranges and all ranges formed therein or thereby.

It is to be appreciated that films having various basis weights can be used in accordance with the present disclosure. For example, some films may have a basis weight of at least about 8 gsm, 12 gsm, 16 gsm, 20 gsm, 25 gsm, 30 gsm, 40 gsm, or 60 gsm. Some films may have basis weight of about 8 gsm to about 60 gsm, specifically reciting all 1 gsm increments within the above-recited ranges and all ranges formed therein or thereby.

Components of the disposable absorbent articles (i.e., diaper, disposable pant, adult incontinence article, sanitary napkin, pantiliner, etc.) described in this specification can at least partially be comprised of bio-sourced content as described in US 2007/0219521A1 Hird et al published on Sep. 20, 2007, US 2011/0139658A1 Hird et al published on Jun. 16, 2011, US 2011/0139657A1 Hird et al published on Jun. 16, 2011, US 2011/0152812A1 Hird et al published on Jun. 23, 2011, US 2011/0139662A1 Hird et al published on Jun. 16, 2011, and US 2011/0139659A1 Hird et al published on Jun. 16, 2011. These components include, but are not limited to, topsheet nonwovens, backsheet films, backsheet nonwovens, side panel nonwovens, barrier leg cuff nonwovens, super absorbent, nonwoven acquisition layers, core wrap nonwovens, adhesives, fastener hooks, and fastener landing zone nonwovens and film bases. In at least one embodiment, a disposable absorbent article component comprises a bio-based content value from about 10% to about 100% using ASTM D6866-10, method B, in another embodiment, from about 25% to about 75%, and in yet another embodiment, from about 50% to about 60% using ASTM D6866-10, method B. In order to apply the methodology of ASTM D6866-10 to determine the bio-based content of any disposable absorbent article component, a representative sample of the disposable absorbent article component must be obtained for testing. In at least one embodiment, the disposable absorbent article component can be ground into particulates less than about 20 mesh using known grinding methods (e.g., Wiley® mill), and a representative sample of suitable mass taken from the randomly mixed particles.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The term "taped diaper" (also referred to as "open diaper") refers to disposable absorbent articles having an initial front waist region and an initial back waist region that are not fastened, pre-fastened, or connected to each other as packaged, prior to being applied to the wearer. A taped diaper may be folded about the lateral centerline with the interior of one waist region in surface to surface contact with the interior of the opposing waist region without fastening or joining the waist regions together. Example taped diapers are disclosed in various suitable configurations in U.S. Pat. Nos. 5,167,897, 5,360,420, 5,599,335, 5,643,588, 5,674,216, 5,702,551, 5,968,025, 6,107,537, 6,118,041, 6,153,209, 6,410,129, 6,426,444, 6,586,652, 6,627,787, 6,617,016, 6,825,393, and 6,861,571; and U.S. Patent Publication Nos. 2013/0072887 A1; 2013/0211356 A1; and 2013/0306226 A1, which are all incorporated by reference herein.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed or pre-fastened by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed). Example diaper pants in various configurations are disclosed in U.S. Pat. Nos. 4,940,464; 5,092,861; 5,246,433; 5,569,234; 5,897,545; 5,957,908; 6,120,487; 6,120,489; 7,569,039 and U.S. Patent Publication Nos. 2003/0233082 A1; 2005/0107764 A1, 2012/0061016 A1, 2012/0061015 A1; 2013/0255861 A1; 2013/0255862 A1; 2013/0255863 A1; 2013/0255864 A1; and 2013/0255865 A1, all of which are incorporated by reference herein.

For the purposes of a specific illustration, FIGS. 1A and 1B show an example of an absorbent article 100 in accordance with the present disclosure. In particular, FIG. 1A shows one example of a plan view of an absorbent article 100 configured as a taped diaper 100T, with the portion of the absorbent article that faces away from a wearer oriented towards the viewer. FIG. 1B shows a plan view of the absorbent article 100 with the portion of the absorbent article that faces toward a wearer oriented towards the viewer. The taped diaper 100T shown in FIGS. 1A and 1B includes an absorbent chassis 102, first and second rear side panels 104 and 106; and first and second front side panels 108 and 110.

As shown in FIGS. 1A and 1B, the absorbent article 100 and the chassis 102 each include a first waist region 116, a second waist region 118, and a crotch region 119 disposed intermediate the first and second waist regions. The first waist region 116 may be configured as a front waist region, and the second waist region 118 may be configured as a back waist region. In some embodiments, the length of each of the front waist region, back waist region, and crotch region may be ⅓ of the length of the absorbent article 100. The absorbent article may also include a laterally extending front waist edge 120 in the front waist region 116 and a longitudinally opposing and laterally extending back waist edge 122 in the back waist region 118. To provide a frame of reference for the present discussion, the diaper 100T in FIGS. 1A and 1B is shown with a longitudinal axis 124 and a lateral axis 126. The longitudinal axis 124 may extend through a midpoint of the front waist edge 120 and through a midpoint of the back waist edge 122. And the lateral axis 126 may extend through a midpoint of a first longitudinal or right side edge 128 and through a midpoint of a second longitudinal or left side edge 130.

As shown in FIGS. 1A and 1B, the absorbent article 100 includes an interior surface 132 (i.e., wearer facing), and an outer, exterior surface 134 (i.e., garment facing). As such, it is also to be appreciated that the various components of the absorbent article described below may each include inner, wearer facing surfaces 132, and an outer, garment facing surfaces 134. The chassis 102 may include a backsheet 136 and a topsheet 138. The chassis 102 may also include an absorbent assembly 140, including an absorbent core 142, disposed between a portion of the topsheet 138 and the backsheet 136. As discussed in more detail below, the absorbent article 100 may also include other features, such as leg elastics and/or leg gasketing elements, waist gasketing element(s), and/or flaps, e.g., side panels and/or ears, to enhance the fits around the legs and waist of the wearer, to enhance the fit around the legs of the wearer.

As shown in FIGS. 1A and 1B, the periphery of the chassis 102 may be defined by the first longitudinal side edge 128. The second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 1A, the laterally extending end edges 144 and 146 may form a portion of the laterally extending front waist edge 120 in the front waist region 116 and a portion of the longitudinally opposing and laterally extending back waist edge 122 in the back waist region 118. The distance between the first lateral end edge 144 and the second lateral end edge 146 may define a pitch length, PL, of the chassis 102. When the absorbent article 100 is worn on the lower torso of a wearer, the front waist edge 120 and the back waist edge 122 may encircle a portion of the waist of the wearer. At the same time, the side edges 128 and 130 may encircle at least a portion of the legs of the wearer. The crotch region 119 may be generally positioned between the legs of the wearer with the absorbent core 142 extending from the front waist region 116 through the crotch region 119 to the back waist region 118.

It is to also be appreciated that a portion or the whole of the absorbent article 100 may also be made laterally extensible. The additional extensibility may help allow the absorbent article 100 to conform to the body of a wearer during movement by the wearer. The additional extensibility may also help, for example, the user of the absorbent article 100, including a chassis 102 having a particular size before extension, to extend the front waist region 116, the back waist region 118, or both waist regions of the absorbent article 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the absorbent article 100 may include a backsheet 136. The backsheet 136 may also define the outer surface 134 of the chassis 102. The backsheet 136 may be impervious to fluids (e.g., menses, urine, and/or runny feces) and may be manufactured in part from a thin plastic film, although other flexible, liquid impervious materials may also be used. The backsheet 136 may prevent the exudates absorbed and contained in the absorbent core from wetting articles which contact the absorbent article 100, such as bedsheets, pajamas and undergarments. The backsheet 136 may also comprise a woven or nonwoven material, polymeric films such as thermoplastic films of polyethylene or polypropylene, and/or multi-layer or composite materials comprising a film and a nonwoven material (e.g., having an inner film layer and an outer nonwoven layer). The backsheet 136 may also comprise an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the absorbent article 100.

Also described above, the absorbent article 100 may include a topsheet 138. The topsheet 138 may also define all or part of the inner surface 132 of the chassis 102. The topsheet 138 may be compliant, soft feeling, and nonirritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539, which are all incorporated by reference herein.

As mentioned above, the absorbent article 100 may also include an absorbent assembly 140 that is joined to the chassis 102. As shown in FIGS. 1A and 1B, the absorbent assembly 140 may have a laterally extending front edge 148 in the front waist region 116 and may have a longitudinally opposing and laterally extending back edge 150 in the back waist region 118. The absorbent assembly 140 may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735, which are all incorporated by reference herein.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprise primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 A1 and 2004/0097895 A1, which are all incorporated by reference herein.

As previously mentioned, the absorbent article 100 may also include elasticized leg gasketing elements 156 and a waist gasketing element 158. It is to be appreciated that the leg gasketing elements 156 can be and are sometimes also referred to as leg bands, side flaps, barrier cuffs, elastic cuffs, leg gasketing systems, or gasketing cuffs. The elasticized leg gasketing elements 156 may be configured in various ways to help reduce the leakage of body exudates in the leg regions. Example leg gasketing elements 156 may include those described in U.S. Pat. Nos. 3,860,003; 4,909,803; 4,695,278; 4,795,454; 4,704,115; and U.S. Patent Publication No. 2009/0312730 A1, which are all incorporated by reference herein.

As shown in FIG. 1B, the chassis 102 may include longitudinally extending and laterally opposing leg gasketing elements 156 that are disposed on the interior surface 132 of the chassis 102 that faces inwardly toward the wearer and contacts the wearer. Each leg gasketing element 156 may have a proximal edge 182 and a distal edge 184. Each leg gasketing element 156 may also have a first side edge 186 and a second side edge 188. The leg gasketing elements may also overlap the absorbent assembly 140, wherein the second side edges 188 extend laterally inward of the respective side edges 152 and 154 of the absorbent assembly. In some configurations, the leg gasketing elements 156 may not overlap the absorbent assembly. It is to be appreciated that the leg gasketing elements 156 may be formed in various ways, such as for example, by folding portions of the chassis 102 laterally inward, i.e., toward the longitudinal axis 124, to form both the respective leg gasketing elements 156 and the side edges 128 and 130 of the chassis 102. In another example, the leg gasketing elements 156 may be formed by attaching an additional layer or layers to the chassis at or adjacent to each of the respective side edges and of the chassis. Each of the leg gasketing elements 156 may be joined to the interior surface 132 of the chassis and/or the absorbent assembly in leg gasketing element attachment zones in the front waist region 116 and in leg gasketing element attachment zones in the back waist region 118. The leg gasketing elements 156 may extend to the same longitudinal extent as the absorbent article 100 or alternatively the leg gasketing elements 156 may have a longitudinal extent that is less than the absorbent article 100.

The waist gasketing element 158 may provide improved fit and containment and may be a portion or zone of the absorbent article 100 that may elastically expand and contract to dynamically fit a wearer's waist. The waist gasketing element 158 may comprise a laterally extending proximal end edge 174 and a longitudinally opposing and laterally extending distal end edge 176. The waist gasketing element 158 may also have a first side edge 178 and a second side edge 180. Both side edges 178 and 180 extend longitudinally between the proximal end edge 174 and the distal end edge 176. The waist gasketing element 158 may be constructed in a number of different configurations including those described in U.S. Pat. Nos. 4,515,595 and 5,151,092, which are all incorporated by reference herein.

Figure 6:
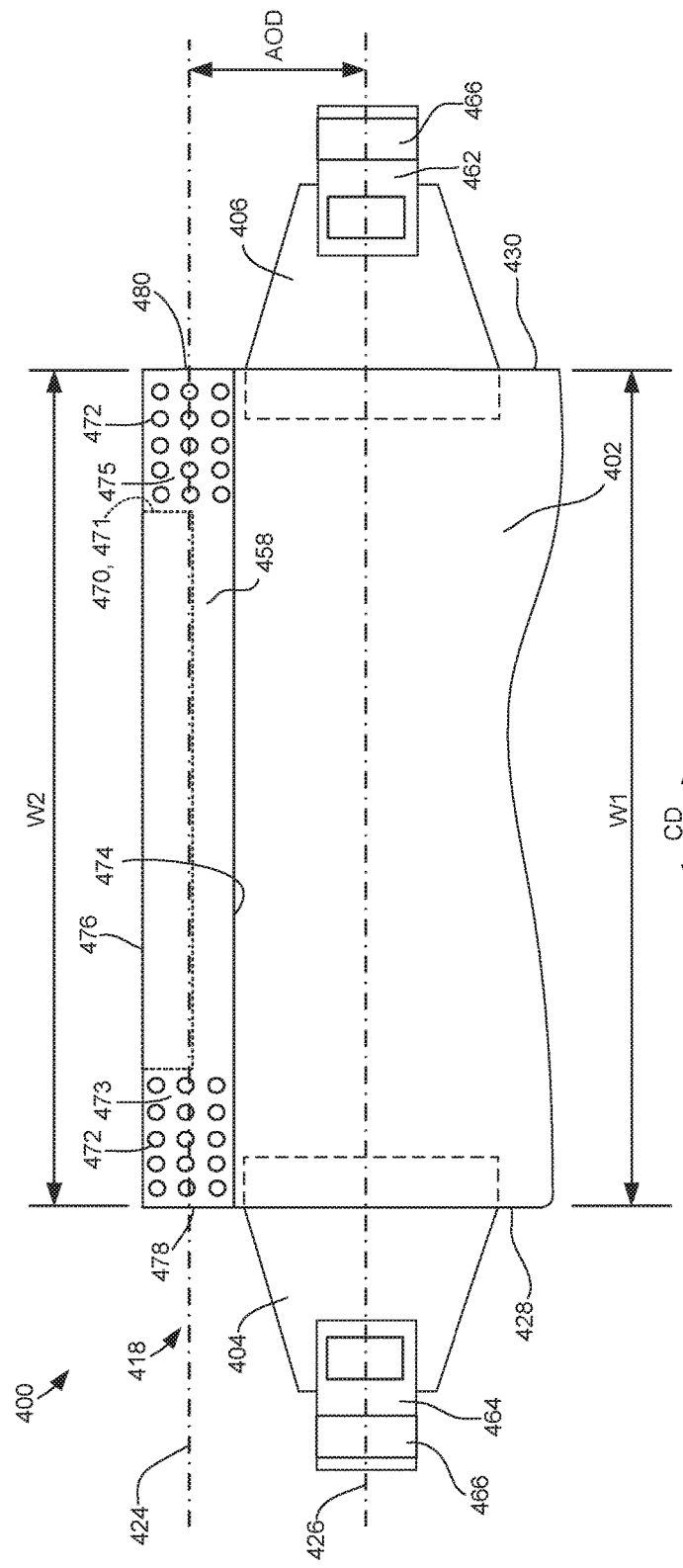
FIG. 6 is a plan view of a back waist region of an absorbent article with the portion of the absorbent article that faces toward a wearer oriented towards the viewer in accordance with another embodiment.

It is to be appreciated that the waist gasketing element 158 may be located in various positions relative to various diaper components. For example, the waist gasketing element 158 may be positioned longitudinally inwardly from the waist edges 120, 122 of the absorbent article and/or toward the lateral edges 148, 150 (FIG. 1A) of the absorbent core 142. In some configurations, the waist gasketing element 158 may be positioned with a lateral edge that is coterminous with the waist edges 120, 122, an example of which is shown in FIG. 6. In some configurations, the waist gasketing element 158 may be positioned such that laterally opposing end regions of the waist gasketing element 158 are located laterally inward from the leg gasketing elements 156. In some configurations, the waist gasketing element 158 may be positioned such that laterally opposing end regions of the waist gasketing element 158 overlap the leg gasketing elements 156. In some configurations, the waist gasketing element 158 may be positioned on the wearer facing surface 132 of the topsheet 138. In some configurations, the waist gasketing element 158 may be positioned on the wearer facing surfaces 132 of the topsheet 138 and the leg gasketing elements 156. In some configurations, the waist gasketing element 158 may be positioned on the wearer facing surfaces 132 of the topsheet 138, and laterally opposing end regions of the waist gasketing element 158 may be positioned between the leg gasketing elements 156 and the topsheet 138. In some configurations, the waist gasketing element 158 may be positioned on the garment facing service 134 of the backsheet 136. The absorbent article 100 may also include more than one waist gasketing element 158, as shown in FIG. 1B, for example, having one waistband 158 positioned in the back waist region 118 and one waistband 158 positioned in the front waist region 116, although other embodiments may be constructed with a single waist gasketing element 158.

At least a portion of the waist gasketing element 158 may be attached to the chassis 102 with an adhesive 170. The waist gasketing element 158 can define at least one adhesive zone 171 of adhesive 170 on the surface of the waist gasketing element 158 that adheres to the chassis 102. It is to be appreciated that the adhesive zone 171 of adhesive 170 may define various sizes and shapes relative to the waist gasketing element 158. For example, as shown in FIG. 1B, the adhesive zone 171 may extend in the cross direction CD for less than the entire width W of the waist gasketing element 158. In some configurations, the adhesive zone 171 may be positioned only on a central region 190 of the waist gasketing element 158 such that adhesive 170 is only provided in the central region 190, and other regions of the waist gasketing element 158 are not adhesively bonded to the chassis 102. In another embodiment, the adhesive zone 171 may extend in the machine direction for the entire length L (FIG. 1B) of the waist gasketing element 158 such that the adhesive is coterminous with the proximal end edge 174 and the distal end edge 176. One or more other portions of the waist gasketing element 158 may be mechanically attached to one or more substrates of the absorbent article 100 using mechanical bonds 172. For example, portions of the waist gasketing element 158 can be attached to the leg gasketing elements 156 using the mechanical bonds 172. The waist gasketing element 158 can therefore define at least a first adhesive-free zone 173 and a second adhesive-free zone 175 and the mechanical bonds 172 may be positioned within the first and second adhesive-free zones 173 and 175. It is to be appreciated that the first and second adhesive free zones 173 and 175 may define various sizes and shapes relative to the waist gasketing element 158. For example, as shown in FIG. 1B, the first adhesive-free zone 173 may laterally extend inward from the first side edge 178 towards the adhesive zone 171 and longitudinally extend from the proximal end edge 174 to the distal end edge 176. The second adhesive-free zone 175 may laterally extend inward from the second side edge 180 towards the adhesive zone 171 and longitudinally extend from the proximal end edge 174 to the distal end edge 176. In some configurations, the first and second adhesive free zones 173, 175 may be positioned laterally inward from the first side edge 178 and the second side edge 180, and in turn, adhesive zones may extend laterally outward from first and second adhesive free zones 173, 175 to or adjacent to the first side edge 178 and the second side edge 180. As described in more detail below, the waist gasketing element 158 may also define one or more adhesive-free zones that do not include mechanical bonds 172. For example, an adhesive-free zone may extend longitudinally from the proximal end edge 174 of the waist gasketing element 158 towards the adhesive zone 171 and extends laterally in the CD for less than the entire width W, therefore forming a pocket between the waist gasketing element 158 and the chassis 102. It is also to be appreciated that in some configurations, the waist gasketing element 158 may be attached to the chassis 102 with only mechanical bonds and without the use of adhesive.

Taped diapers may be manufactured and provided to consumers in a configuration wherein the front waist region and the back waist region are not fastened, pre-fastened, or connected to each other as packaged, prior to being applied to the wearer. For example, the taped diaper 100T may be folded about a lateral centerline with the interior surface 132 of the first waist region 116 in surface to surface contact with the interior surface 132 of the second waist region 118 without fastening or joining the waist regions together. The rear side panels 104 and 106 and/or the front side panels 108 and 110 and/or the leg gasketing elements 156 may also be folded laterally inward toward the inner surfaces 132 of the waist regions 116 and 118.

The absorbent article 100 may also include various configurations of fastening elements to enable fastening of the front waist region 116 and the back waist region 118 together to form a closed waist circumference and leg openings once the absorbent article is positioned on a wearer. For example, as shown in FIGS. 1A and 1B, the absorbent article 100 may include first and second fastening members 162, 164, also referred to as tabs, connected with the first and second rear side panels 104, 106, respectively. The absorbent article may also include first and second front side panels 108, 110, that may or may not include fastening members.

With continued reference to FIGS. 1A and 1B, each side panel 104, 106 and/or fastening member 162 and 164 may form a portion of or may be permanently bonded, adhered or otherwise joined directly or indirectly to the chassis 102 laterally inward from the side edges 128 and 130, in one of the front waist region 116 or the back waist region 118. Alternatively, the fastening members 162, 164 may form a portion of or may be permanently bonded, adhered or otherwise joined directly or indirectly to the first and second rear panels 104, 106 at or adjacent the distal edge of the panel and/or the first and second front side panels 108 and 110 at or adjacent the distal edge of the side panel. It is to be appreciated that the fastening members and/or side panels may be assembled in various ways, such as disclosed for example, in U.S. Pat. No. 7,371,302, which is incorporated by reference herein. The fastening members 162, 164 and/or side panels 104, 106, 108, 110 may also be permanently bonded or joined at or adjacent the side edges 128 and 130 of the chassis 102 in various ways, such as for example, by adhesive bonds, sonic bonds, pressure bonds, thermal bonds or combinations thereof, such as disclosed for example, U.S. Pat. No. 5,702,551, which is incorporated by reference herein.

Referring now to FIG. 1B, the first fastening member 162 and/or the second fastening member 164 may include various types of releasably engageable fasteners. The first and second fastening members 162 and/or 164 may also include various types of refastenable fastening structures. For example, the first and second fastening members 162 and 164 may include mechanical fasteners 166, in the form of hook and loop fasteners, hook and hook fasteners, macro-fasteners, buttons, snaps, tab and slot fasteners, tape fasteners, adhesive fasteners, cohesive fasteners, magnetic fasteners, hermaphroditic fasteners, and the like. Some examples of fastening systems and/or fastening members 162, 164 are discussed in U.S. Pat. Nos. 3,848,594; 4,662,875; 4,846, 815; 4,894,060; 4,946,527; 5,151,092; 5,221,274; 6,251, 097; 6,669,618; 6,432,098; and U.S. Patent Publication Nos. 2007/0078427 A1 and 2007/0093769 A1, which are all incorporated by reference herein.

As previously mentioned, the fastening members 162 and 164 may be constructed from various materials and may be constructed as a laminate structure. The fastening members 162 and 164 may also be adapted to releasably and/or refastenably engage or connect with another portion of the diaper 100. For example, as shown in FIG. 1A, the diaper 100 may include a connection zone 168, sometimes referred to as a landing zone, in the first waist region 116. As such, when the taped diaper 100 is placed on a wearer, the fastening members 162 and 164 may be pulled around the waist of the wearer and connected with the connection zone 168 in the first waist region 116 to form a closed waist circumference and a pair of laterally opposing leg openings. It is to be appreciated that the connection zone may be constructed from a separate substrate that is connected with the chassis 102 of the taped diaper. In some embodiments, the connection zone may be integrally formed as part of the backsheet 136 of the diaper 100 or may be formed as part of the first and second front panels 108, 110, such as described in U.S. Pat. Nos. 5,735,840 and 5,928,212, which are both incorporated by reference herein.

FIG. 2 is a plan view of a back waist region of another example absorbent article 200 with the portion of the absorbent article that faces toward a wearer oriented towards the viewer. FIG. 3 is a cross-sectional view of FIG. 2 taken along line 3-3. Referring to FIGS. 2 and 3, and similarly to the absorbent article 100 of FIGS. 1A and 1B, the absorbent article 200 includes a chassis 202 having a back waist edge 222 and side edges 228 and 230. The chassis 202 may include a backsheet 236 and a topsheet 238, as well as intermediate layers or materials, such as a polymeric backsheet film 235 and an absorbent assembly 240.

The absorbent article 200 also includes a waist gasketing element 258, which is schematically illustrated to include a laminate of an elastic film 220 bonded with a first nonwoven 216 and a second nonwoven 218. The first nonwoven 216 may be bonded to the second nonwoven 218 through any suitable technique, such as ultrasonic bonding, adhesive bonding, and so forth. One or both of the nonwovens 216 and 218 may be, for example, an elastomeric nonwoven or a non-elastic nonwoven. It is also be appreciated that the first nonwoven 216 and the second nonwoven 218 may be the same size or may have different sizes and may define the same or different widths and/or lengths. Further, while the waist gasketing element 258 is shown in FIG. 3 to have two layers of nonwovens, it is to be appreciated that this disclosure is not so limited. For example, the continuous elastic substrate may be configured as a bi-laminate with an elastic film bonded with a single nonwoven substrate, such as bi-laminate formed with the elastic film 220 and nonwoven 216. Further, instead of an elastic film 220, the waist gasketing element 258 can comprise elastic strands, or other suitable materials. The laminate of film 220 and one or more non-wovens can be an extrusion bonded laminate. It is also to be appreciated that the waist gasketing element 258 may be assembled in various ways, such as for example, as disclosed in U.S. Pat. Nos. 6,572,595; 6,830,800; 7,087,287; and 7,803,244; and U.S. Patent Publication Nos. 2018/0042778 A1; 2018/0042787 A1; 2018/0042779 A1; and 2018/0042780 A1, which are all incorporated by reference herein.

Mechanical bonds 272 are shown in FIG. 2 and schematically illustrated in FIG. 3 to depict the mechanical connection of the waist gasketing element 258 to the chassis 202. In some configurations, however, the mechanical connection is between the waist gasketing element 258 and leg gasketing elements 256 such that the chassis 202 is not incorporated into the mechanical bonds 272. Furthermore, in some configurations, the waist gasketing element 258 may be mechanically connected to the top sheet 238 but not the backsheet 236. Referring to FIG. 3, mechanical bonds 272 in the illustrated example are shown extending from the first nonwoven 216 to the backsheet 236 and intermediate substrates therebetween, such as leg gasketing elements 256. A first grouping of mechanical bonds 272 may be positioned within a first adhesive-free zone 273 (FIG. 2) and second grouping of mechanical bonds 272 may be positioned within a second adhesive-free zone 275 (FIG. 2). As shown in FIG. 2, the first adhesive-free zone 273 and the second adhesive-free zone 275 may each have a width W1 in the cross direction CD. In accordance with various configurations, the width W1 may be up to 75 mm, or in the range of about 5 mm to about 30 mm, or may be in the range of about 10 mm to about 20 mm, or may be about 15 mm. Each of the first adhesive-free zone 273 and the second adhesive-free zone 275 may extend in the machine direction MD from a proximal end edge 274 to a distal end edge 276 of the waist gasketing element 258. While mechanical bonds 272 may extend through multiple absorbent article components to bond the waist gasketing element 258 (as shown in FIG. 3), the mechanical bonds 272 may extend through just the waist gasketing element 258 and the topsheet 238, or just through waist gasketing element 258 and the leg gasketing elements 256, or just through the waist gasketing element 258, the topsheet 238, and leg gasketing elements 256.

A central portion of the example waist gasketing element 258 is attached to the chassis 202 with an adhesive 270. The waist gasketing element 258 can define at least one adhesive zone 271 of adhesive 270 on the surface of the waist gasketing element 258 that adheres to the chassis 202. As shown in FIG. 2, the adhesive zone 271 may have a width W2 in the cross direction CD and a height H1 in machine direction MD. In accordance with various configurations, the width W2 may be in the range of about 80 mm to about 260 mm, or may be in the range of about 90 mm to about 130 mm, or may be about 120 mm. The height of the waist gasketing element 258 in the machine direction MD is shown as H3. In some configurations, the adhesive zone 271 may extend in the machine direction MD from the proximal end edge 274 of the waist gasketing element 258 to the distal edge 276 of the waist gasketing element 258 such that H1 is substantially equal to H3. In accordance with various configurations, the H1 may be in the range of about 5 mm to about 35 mm, or may be in the range of about 25 mm to about 60 mm, or may be about 40 mm. In accordance with various configurations, the H3 may be in the range of about 10 mm to about 35 mm, or may be in the range of about 25 mm to about 80 mm, or may be about 40 mm. Further, the adhesive zone 271 may be spaced away from the proximal end edge 274 and/or the distal edge 276 of the waist gasketing element 258, including being spaced away by 1 mm, 2 mm, 5 mm, 10 mm, or 15 mm from the proximal end edge 274 and/or the distal edge 276 of the waist gasketing element 258.

As shown in FIG. 2, the example waist gasketing element 258 defines a third adhesive-free zone 275 that has a width W2 in the cross direction CD and a height H2 in the machine direction MD. The third adhesive-free zone 277 may not include any adhesive or mechanical bonds and therefore may be disconnected from the chassis 102. As such, a pocket may be formed between the waist gasketing element 258 and the chassis 102 in that zone. The pocket may be defined in the machine direction MD by the portion of the proximal end edge 274 laterally extending between the first and second adhesive-free zones 273 and 275 and the adhesive zone 271. The pocket may be defined in the cross direction CD by the portion of the waist gasketing element 258 extended between the first and second adhesive-free zones 273 and 275. In accordance with various configurations, the H2 may be in the range of about 10 mm to about 35 mm, or may be in the range of about 25 mm to about 60 mm, or may be about 30 mm.

Figure 4:
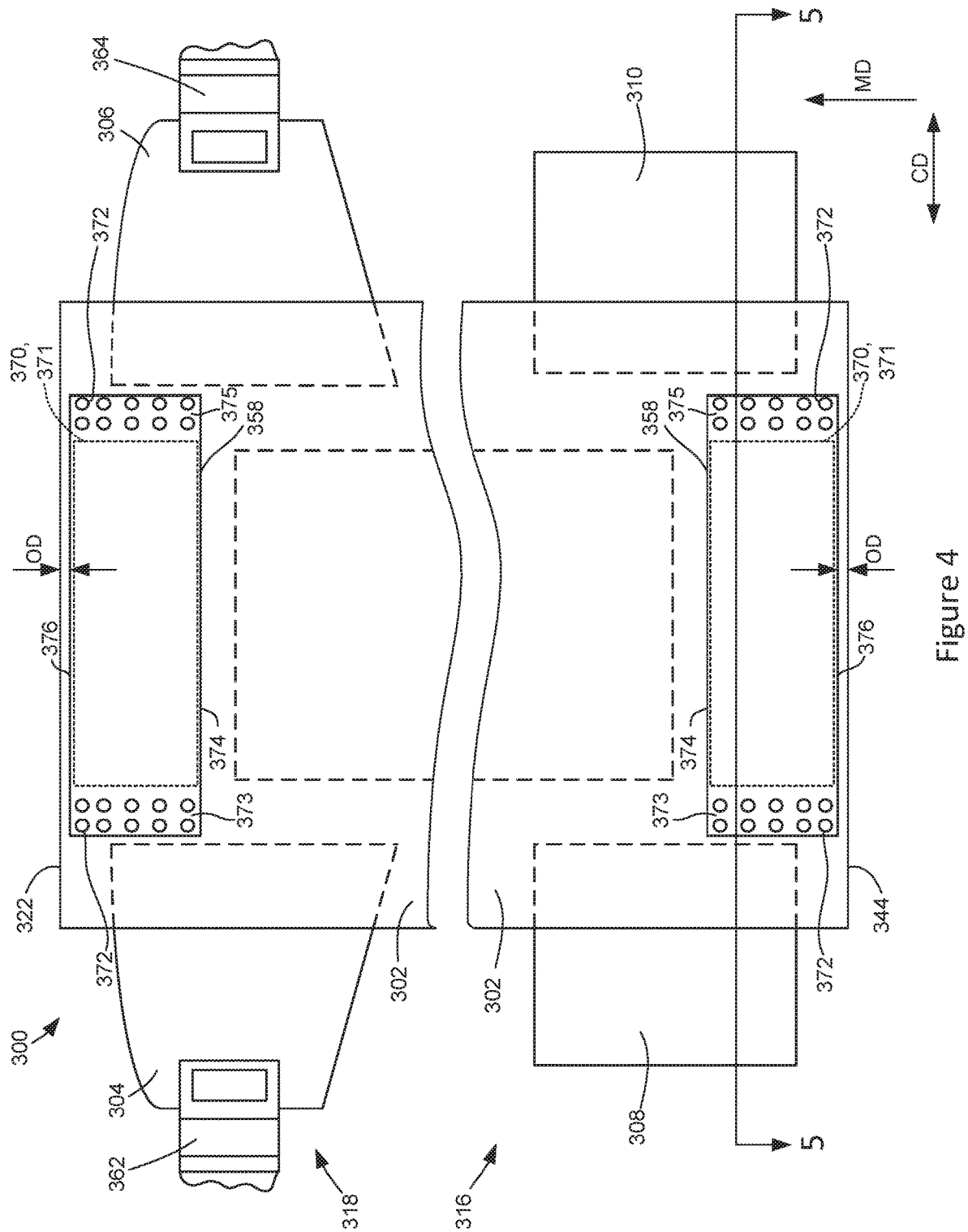
FIG. 4 depicts waist gasketing elements positioned in front and back waist regions of an absorbent article with the portion of the absorbent article that faces toward a wearer oriented towards the viewer.

FIG. 2 depicts an example absorbent article 200 in which the waist gasketing element 258 is positioned such that the distal edge 276 of the waist gasketing element 258 is coterminous with the back waist edge 222. It is to be appreciated, that a waist gasketing element similar to the waist gasketing element 258 can optionally be provided in a front waist region of the absorbent article 200 and similarly positioned conterminously with a front waist edge. However, while the waist gasketing element 258 shown in FIG. 2 is coterminous with the back waist edge 222, this disclosure is not so limited. For example, FIG. 4 is a plan view of a back waist region 318 and a front waist region 316 of an absorbent article 300 with the portion of the absorbent article that faces toward a wearer oriented towards the viewer. The front waist region 316 is shown to have first and second front side panels 308 and 310 and the back waist region 318 is shown to have rear side panels 304 and 306. FIG. 4 depicts waist gasketing elements 358 positioned in the front and back waist regions 316 and 318. Similar to the waist gasketing elements described above, the waist gasketing elements 358 are bonded to a chassis 302 of the absorbent article 300 through mechanical bonds 372 positioned in adhesive-free zones 373 and 375. A central portion of each of the waist gasketing elements 358 is attached to the chassis 302 with an adhesive 370. The waist gasketing elements 358 define an adhesive zone 371 of adhesive 370 on the surface of the waist gasketing element 358 that adheres to the chassis 302. In this example configuration, the adhesive zone 371 extends in the machine direction MD to be coterminous with a proximal end edge 374 and a distal end edge 376 of the waist gasketing elements 358.

Referring now to the back waist region 318, the waist gasketing element 358 is positioned relative to the chassis 302 such that it is offset in the machine direction MD from a back waist edge 322 by an offset distance OD. The offset distance OD 0 mm, such that the distal end edge 376 of the waist gasketing elements 358 positioned in the back waist region 318 is coterminous with back waist edge 322 and waist gasketing elements 358 positioned in the front waist region 316 is coterminous with front waist edge 344. Alternatively, the offset distance OD can be in the range of about 1 mm to about 10 mm, or in the range of about 2 mm to about 5 mm, or in the range of about 5 mm to about 20 mm, or in the range of about 20 mm to about 50 mm, or can be about 10 mm. The waist gasketing element 358 is positioned in the front waist region 316 and may also be offset in the machine direction MD from a front waist edge 344 by an offset distance OD. The offset distance OD can be 0 mm or be in the range of about 1 mm to about 10 mm, or in the range of about 2 mm to about 5 mm, or in the range of about 5 mm to about 20 mm, or in the range of about 20 to about 40 mm, or can be about 10 mm.

Figure 5:
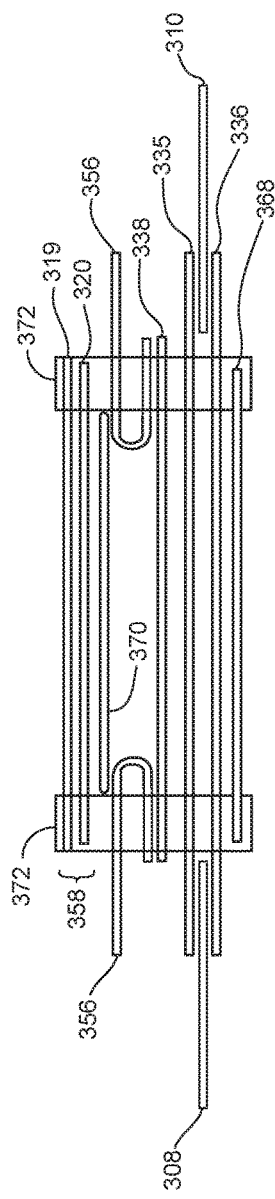
FIG. 5 is a cross-sectional view of absorbent article taken along line 5-5 in FIG. 4.

FIG. 5 is a cross-sectional view of FIG. 4 taken along line 5-5. As shown in FIG. 5, a central portion of the example waist gasketing element 358 is attached to the chassis 302 (FIG. 4) with an adhesive 370. In the illustrated example, the waist gasketing element 558 is schematically illustrated to include a bi-laminate of an elastic film 320 bonded with a nonwoven 319. The absorbent article 300 is shown to include a landing zone 368 that provides a connection zone for the fastening members 362 and 364 (FIG. 4). The fastening members 362 and 364 may be pulled around the waist of the wearer and connected with the landing zone 368 in the front waist region 316 to form a closed waist circumference and a pair of laterally opposing leg openings. In this example configuration, the mechanical bonds 372 extend through the waist gasketing element 358 and the landing zone 368, as well as various intermediate layers, such as leg gasketing elements 356, a polymeric backsheet film 335, and a backsheet 336. Incorporation of the landing zone 368 into the mechanical bonds 372 can beneficially improve strength of the mechanical bonds, and overlap of the landing zone 368 and the waist gasketing element 358 can provide stiffness to prevent or reduce inadvertent flipping of the waist gasketing element 358.

FIG. 5 is a plan view of a back waist region 418 of an absorbent article 400 with the portion of the absorbent article that faces toward a wearer oriented toward the viewer in accordance with another embodiment. The absorbent article 400 includes a chassis 402 that has a first side edge 428 and a second side edge 430. The absorbent article 400 has a width W1 in the cross direction CD as measured laterally between the first and second side edges 428 and 430. A waist gasketing element 458 schematically illustrated in FIG. 4 is attached to the chassis 402 through mechanical bonds 472 positioned in a first adhesive-free zone 473 and a second adhesive-free zone 475. A central portion of the example waist gasketing element 458 is attached to the chassis 402 with an adhesive 470. The waist gasketing element 458 can define at least one adhesive zone 471 of adhesive 470 on the surface of the waist gasketing element 458 that adheres to the chassis 402. The waist gasketing element 458 may comprise a laterally extending proximal end edge 474 and a longitudinally opposing and laterally extending distal end edge 476. The waist gasketing element 458 may also have a first side edge 478 and a second side edge 480. Both side edges 478 and 480 extend longitudinally between the proximal end edge 474 and the distal end edge 476. The waist gasketing element 458 has a width W2 in the cross direction CD as measured laterally between the side edges 478 and 480. In this embodiment, the first side edge 478 is coterminous with the first side edge 428 of the chassis 402 and the second side edge 480 is coterminous with the second side edge 430 of the chassis 402. Accordingly, in this example configuration the width of the back waist region 418 is the same as the width of the waist gasketing element 458, such that W1 is substantially equal to W2.

As shown in FIG. 6, the absorbent article 400 may include first and second fastening members 462, 464, also referred to as tabs, connected with the first and second rear side panels 404, 406, respectively. The first fastening member 462 and/or the second fastening member 464 may include various types of releasably engageable fasteners. The first and second fastening members 462 and/or 464 may also include various types of refastenable fastening structures. For example, the first and second fastening members 462 and 464 may include mechanical fasteners 466, in the form of hook and loop fasteners, hook and hook fasteners, macrofasteners, buttons, snaps, tab and slot fasteners, tape fasteners, adhesive fasteners, cohesive fasteners, magnetic fasteners, hermaphroditic fasteners, and the like.

The first and second fastening members 462, 464 can define a tab axis 426 extending in the cross direction through a longitudinal midpoint of each of the first and second fastening members 462, 464. The tab axis 426 may be parallel to a lateral axis of the absorbent article 400. The waist gasketing element 458 can define a waist gasketing element axis 424 extending in the cross direction through a longitudinal midpoint of the waist gasketing element 458. The waist gasketing element axis 424 may be parallel to the tab axis 426. In accordance with various configurations, the waist gasketing element axis 424 may be offset from the tab axis 426 in a direction towards the distal end edge 476 by an axis offset distance AOD. In FIGS. 6, the tab axis 426 does not overlap any portion of the waist gasketing element 458, but this disclosure is not so limited. In some configurations, for example, the tab axis 426 may overlap a portion of the waist gasketing element 458 in a region located between the waist gasketing element axis 424 and the first side edge 478.

When the fastening members 462 and 464 are pulled around the waist of the wearer and connected with a front waist region to form a closed waist circumference a direct line of tension is formed between the fastening members 462 and 464. Offsetting the waist gasketing element axis 424 from the tab axis 426 by a distance AOD can beneficially keep the waist gasketing element 458 from being aligned with this direct line of tension. Thus, configuring the absorbent article 400 such that the waist gasketing element axis 424 is spaced away from the tab axis 426 may allow for the waist gasketing element 458 to be exposed to less force levels than the levels of force to which the fastening members 462 and 464 are exposed. As a result, the stretchable waist gasketing element axis 424 can retain energy that can be used to close gaps when the wearer bends yet not impact the overall span of the users the article can fit.

Figure 7:
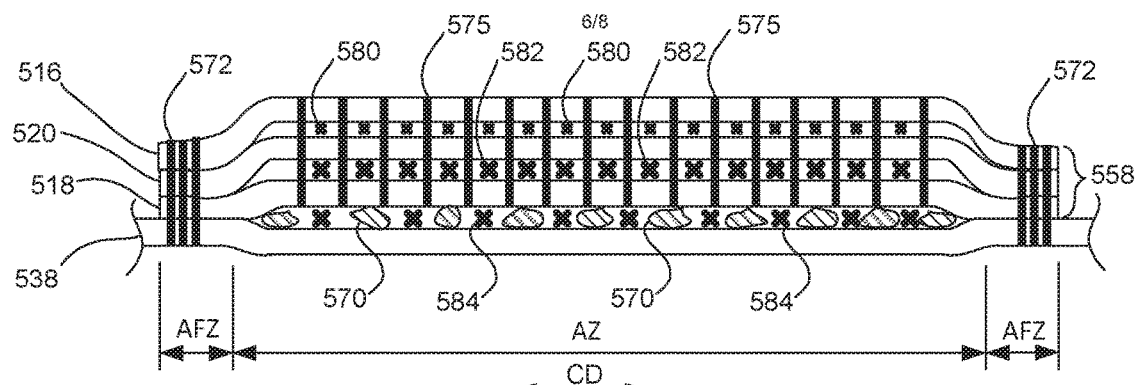
FIG. 7 schematically depicts a cross-sectional view of a waist gasketing element attached to a top sheet that is taken along a lateral axis of an example absorbent article.

Referring now to FIG. 7, a simplified cross-sectional view of a waist gasketing element 558 attached to a top sheet 538 is schematically depicted. The example waist gasketing element 558 is shown to be a laminate of a first nonwoven 516, an elastic film 520, and a second nonwoven 518 that is formed through ultrasonic bonds 575. While ultrasonic bonds 575 are depicted in FIG. 7, any suitable technique for creating the laminate can be utilized. The bond sites can create a plurality of longitudinal channels 580 that are defined between the first nonwoven 516 and the elastic film 520. Another plurality of longitudinal channels 582 may be defined between the elastic film 520 and the second nonwoven 518. Additional description regarding example bond patterns is found below with reference to the bonds 675 depicted in FIGS. 8 and 9.

Still referring to FIG. 7, the waist gasketing element 558 can define a plurality of different zones in the cross direction CD, shown as adhesive-free zones AFZs and an adhesive zone AZ. The adhesive zone AZ is the portion of the waist gasketing element 558 that is adhered to the top sheet 538 via an adhesive 570. The adhesive 570 can be applied to either the waist gasketing element 558 and/or the top sheet 538 in a stripes, or other formations that create gaps or spacings in the lateral direction between adjacent stripes of adhesive. A plurality of longitudinal channels 584 may be defined between the top sheet 538 and the second nonwoven 518. The plurality of longitudinal channels 580, 582, and 584, sometimes referred to a microchannels, can be formed when the elasticized waist gasketing element 558 is relaxed. The plurality of longitudinal channels 580, 582, and 584 can define an inboard opening at a proximal end edge of the waist gasketing element (such as proximal end edge 474 in FIG. 6) and an outboard opening at the distal end edge (such as distal end edge 476 in FIG. 6) of the waist gasketing element. The plurality of longitudinal channels 580, 582, and 584 can beneficially trap menses, urine, and/or runny feces.

Figure 8:
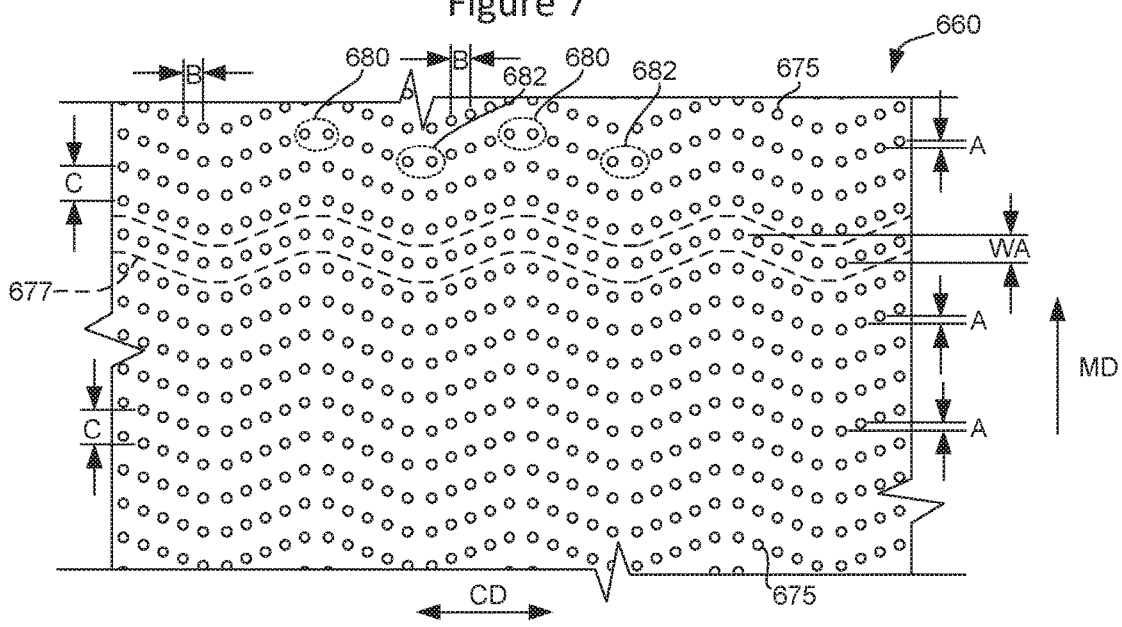
FIG. 8 is a schematic top view of a laminate that can be cut in the cross direction to form waist gasketing elements.
Figure 9:
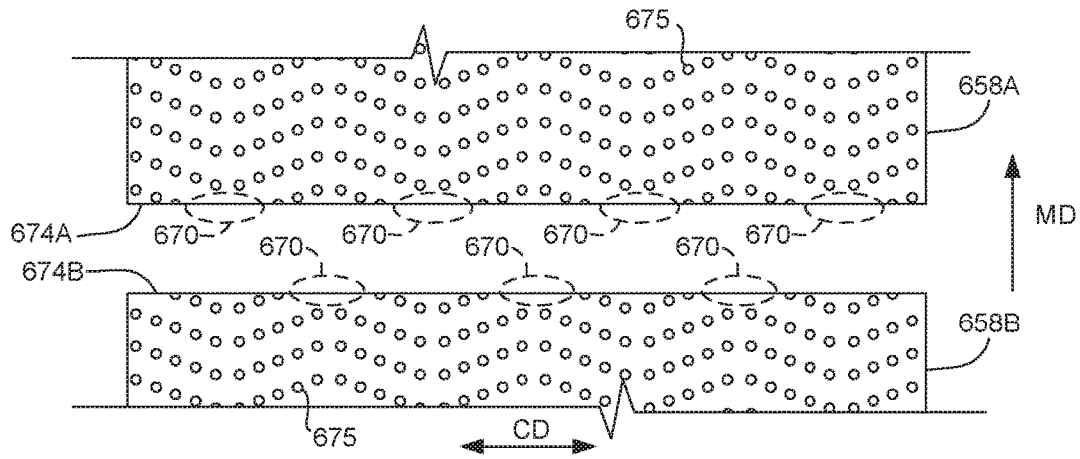
FIG. 9 depicts the laminate of FIG. 8 subsequent to a knife cut in the cross direction, thereby forming waist gasketing elements, which are shown spaced apart in the machine direction.

FIG. 8 is a schematic top view of a laminate 660 that can be cut in the cross direction to form waist gasketing elements. FIG. 9 depicts the laminate 660 subsequent to cutting in the cross direction, thereby forming waist gasketing elements 658A and 658B, which are shown spaced apart in the machine direction 658 to show the end edges 674A and 674B that are formed subsequent to cutting. An example bond pattern having a plurality of bond sites 675 is shown in FIGS. 8 and 9. As is to be appreciated, the bond sites 675 can be used to bond various layers such as a film, and one or more non-wovens, to form a laminate. The arrangement of bond sites 675 can be configured to reduce the formation of an unwanted lip or flange across the entire end edges 674A, 674B. As shown in FIG. 9, while the end edges 674A, 674B are shown to have small bond-free portions 670, such bond-free portions 670 are disposed intermittently across the end edges 674A, 674B, with other portions of the end edges 674A, 674B having bonds.

The example arrangement of bond sites 675 illustrated in FIGS. 8 and 9 generally shows a wavy pattern of bond sites 675. While the bond sites 675 are shown in a wavy pattern, other patterns can be used to provide the same benefits, such as, for example, a zig-zag pattern or other suitable repeating pattern, having an amplitude that at least about half the distance between consecutive bond sites in the machine direction MD.

As shown in FIG. 8, the bond sites 675 can form a plurality of waves 677 that each extend in the cross direction CD and have peaks 680 and valleys 682. The waves 677 may have an amplitude (shown as wave amplitude WA) that is just slightly less than the MD spacing of the bond sites 675 (shown as dimension C). In some configurations, the waist gasketing element 658A can be attached to an absorbent article in a back waist region such that one of the peaks 680 is generally centered on the back of a wearer of the absorbent article. The waist gasketing element 658B can be attached to the absorbent article in a front waist region such that one of the valleys 682 is generally centered on the front of the wearer of the absorbent article. In accordance with the illustrated embodiment, each peak 680 may in include two adjacent bond sites 675 that are laterally spaced in the cross direction along the same lateral axis. Similarly, each valley 682 may include two bond sites 675 that are laterally spaced in the cross direction along the same lateral axis.

The bond sites 675 connecting each peak 680 and valley 672 may be spaced in the machine direction by a distance A. The distance A may in the range of about 0.1 mm to about 1 mm, or in the range of about 1 mm to about 3 mm, or in the range of about 2 to about 10 mm. In some embodiments, the distance A is about 0.5 mm. Laterally adjacent bond sites 675 in a wave can be separated in the cross direction CD by a distance B. The distance B may in the range of about 2 mm to about 6 mm. The distance B may in the range of about 3 mm to about 5 mm, or about 5 mm to about 15 mm. In some embodiments, the distance B is about 4.8 mm. Longitudinally adjacent bond sites 675 in a consecutive waves can be separated in the machine direction MD by a distance C. The distance C may in the range of about 2 mm to about 10 mm. The distance C may in the range of about 7 mm to about 20 mm. In some embodiments, the distance C is about 4 mm.

Figure 10:
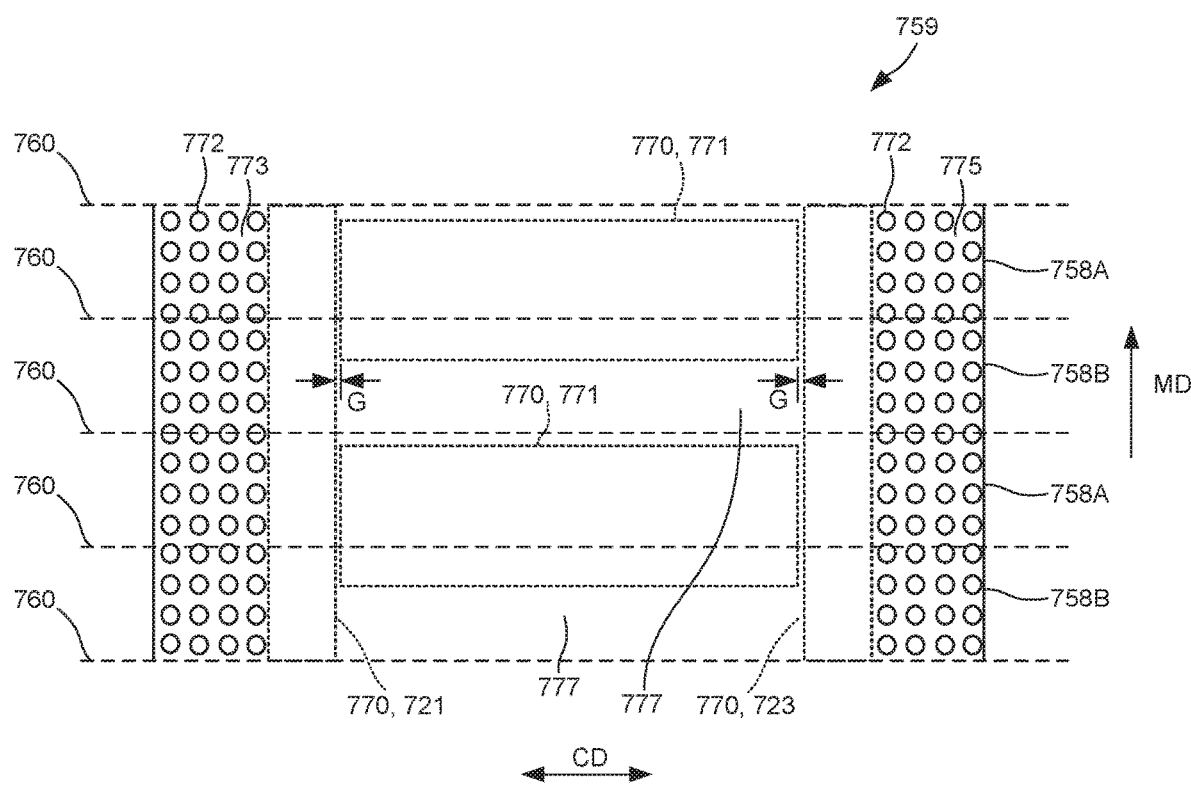
FIG. 10 schematically depicts an example waist gasketing laminate prior to separation at a cutting locations.

Referring now to FIG. 10, an example waist gasketing laminate 759 prior to separation at cut locations 760 is schematically illustrated. Subsequent to separation, waist gasketing elements 758A and 758B are formed and can be applied to a chassis of an absorbent article. Similar to various waist gasketing element described above, the waist gasketing laminate 759 can define a plurality of different zones in the cross direction CD. An adhesive zone 771 is a portion of the waist gasketing laminate 759 that is adhered to a chassis of an absorbent article via an adhesive 770. A first adhesive-free zone 773 and a second adhesive-free zone 775 are the portions of the waist gasketing laminate 759 that may be bonded to a chassis of an absorbent article via mechanical bonds 772, as described above. In this example configuration, however, the waist gasketing laminate 759 also includes a first end adhesive portion 721 and a second end adhesive portion 723. An adhesive 770 may be used in the first end adhesive portion 721 and the second end adhesive portion 723 to adhere those portions to a chassis of an absorbent article.

The first end adhesive portion 721 may be positioned in the cross direction CD between the first adhesive-free zone 773 and the adhesive zone 771. The second end adhesive portion 723 may be positioned in the cross direction CD between the adhesive zone 771 and the second adhesive-free zone 775. As shown, the first and second end adhesive portions 721 and 723 may extend in the machine direction MD the entire longitudinal length of the waist gasketing elements 758A and 758B. The application of the adhesive 770 in the first and second end adhesive portions 721 and 723 can beneficially improve the total strength of the mechanical bonds 772, especially when the mechanical bonds 772 are relatively small and have an open pattern.

In some configurations, the width of the first end adhesive portion 721 and a second end adhesive portion 723 in the machine direction is reduced in order to increase the width of an adhesive free zone 777, sometimes referred to as a pocket, that is positioned therebetween. During production of the waist gasketing laminate 759, the adhesive 770 can be applied continuously to the laminate in the first end adhesive portion 721 and the second end adhesive portion 723, while the adhesive 770 applied to the adhesive zone 771 can be applied intermittently. Due to the use of two different adhesive delivery assemblies, a small gap Gin the cross direction CD may be defined between the adhesive zone 771 and each of the first and second end adhesive portions 721 and 723. However, while a gap G is depicted for illustration purpose, this gap may or may not exist as a result of the specific adhesive application that is used. Furthermore, the adhesives in any of the portions 721, 723, and 771 can be applied to the waistband gasketing laminate 759 or can be applied to the chassis.

Figure 11:
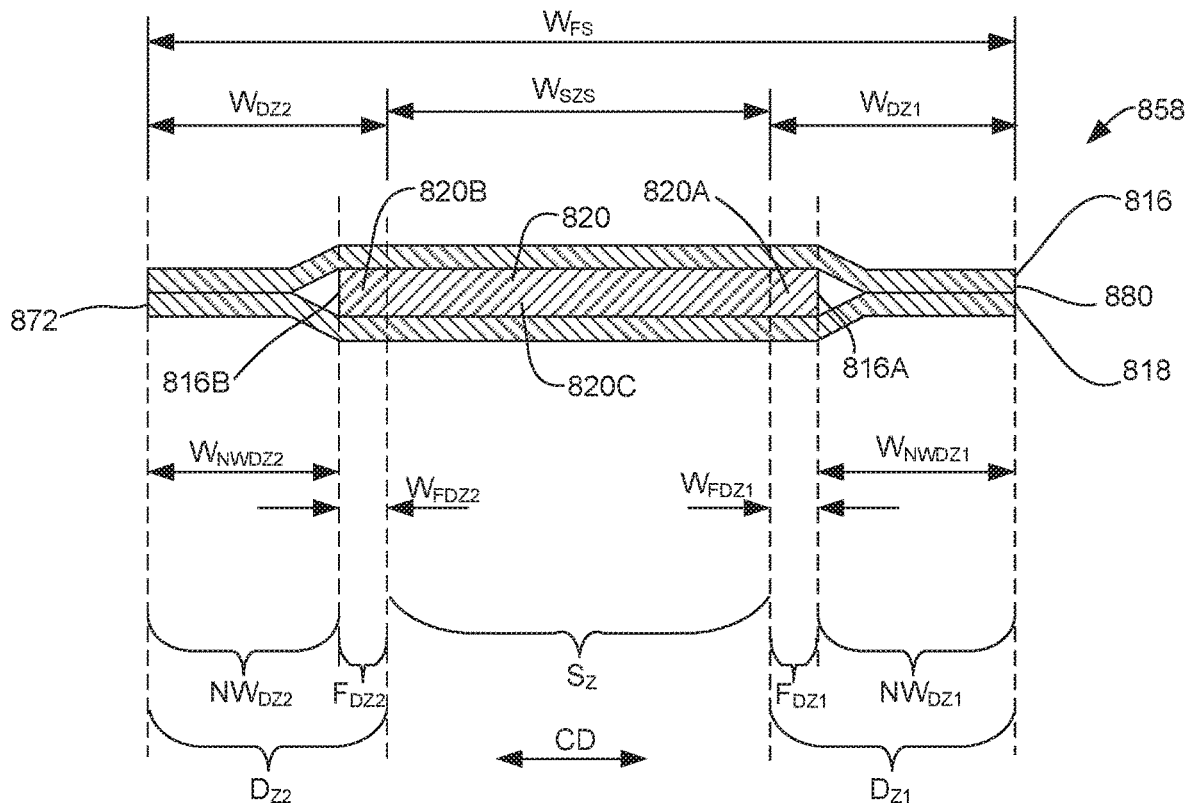
FIG. 11 shows a cross-sectional view of example waist gasketing element taken in the machine direction.
Figure 12:
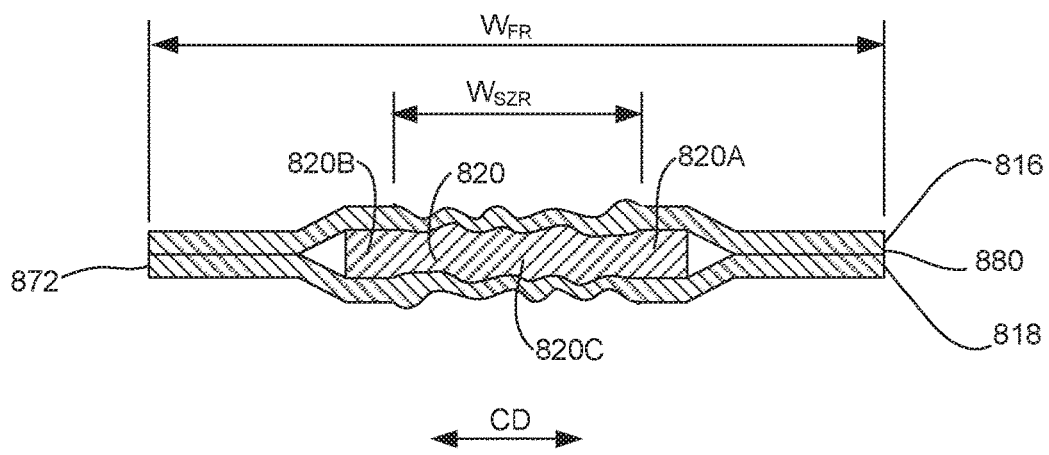
FIG. 12 depicts the waist gasketing element from FIG. 11 in a relaxed, contracted condition.

Referring now to FIG. 11, a cross-sectional view of example waist gasketing element 858 taken in the machine direction is shown in a fully stretched condition. FIG. 12 depicts the waist gasketing element 858 from FIG. 11 in a relaxed, contracted condition. The waist gasketing element 858 can be attached to an absorbent article through a combination of mechanical bonds and adhesive, in accordance with present disclosure. The waist gasketing element 858 can include an elastic film 820. The elastic film 820 may include a first edge region 820A adjacent a first edge 816A and a second edge region 820B adjacent a second edge 816B. The first edge region 820A is separated from the second edge region 820B in the cross direction CD by a central region 820C. During assembly of the waist gasketing element 858 some portions of the first and second edge regions 820A and 820B of the elastic film 820 may remain unstretched in the cross direction CD. Thus, as shown in FIG. 11, the waist gasketing element 858 may include a first film dead zone $F_{DZ1}$ and a second film dead zone $F_{DZ2}$ that may correspond with the unstretched regions of the elastic film 820. In addition, the waist gasketing element 858 may also include a first nonwoven dead zone $NW_{DZ1}$ and a second nonwoven dead zone $NW_{DZ2}$ that correspond with regions where the elastic film 820 is not positioned between the first substrate 816 and the second substrate 818. The first nonwoven dead zone $NW_{DZ1}$ may extend from a first longitudinal edge 880 of the waist gasketing element 858 to the first film dead zone $F_{DZ1}$, and the second nonwoven dead zone $NW_{DZ2}$ may extend from the second longitudinal edge 872 of the waist gasketing element 858 to the second film dead zone $F_{DZ2}$. As such, the waist gasketing element 858 may not be elastomeric in the cross direction CD in the nonwoven dead zones $NW_{DZ1}$, $NW_{DZ2}$ and the film dead zones $F_{DZ1}$, $F_{DZ2}$.

With continued reference to FIG. 11, the waist gasketing element 858 may include a stretch zone $S_Z$ located between the nonwoven dead zones $NW_{DZ1}$, $NW_{DZ2}$ and the film dead zones $F_{DZ1}$, $F_{DZ2}$. The waist gasketing element 858 may be elastomeric in the cross direction CD in the stretch zone $S_Z$. As shown in FIGS. 11 and 12, the waist gasketing element 858 may define a width $W_{FS}$ when fully stretched in the cross direction CD (FIG. 10), and the waist gasketing element 858 may define a width $W_{FR}$ when fully relaxed in the cross direction CD (FIG. 11), wherein $W_{FR}$ is less than $W_{FS}$. Similarly, the stretch zone $S_Z$ may define a width $W_{SZS}$ when fully stretched in the cross direction CD (FIG. 11), and the stretch zone $S_Z$ may define a width $W_{SZR}$ when fully relaxed in the cross direction CD (FIG. 12), wherein $W_{SZR}$ is less than $W_{SZS}$. In some configurations, the width of the adhesive zone 271 in the cross direction CD adhesive zone in fully stretched condition may be equal to or less than the width $W_{SZS}$. It is to be appreciated that the width $W_{SZR}$ and the width $W_{SZS}$ may define have various relative sizes with respect to each other. For example, in some configurations, a ratio of $W_{SZS}/W_{SZr}$ may be from about 1.3 to about 4, specifically reciting all 0.1 increments within the above-recited ranges and all ranges formed therein or thereby. It is to be appreciated that the width $W_{FR}$ and the width $W_{FS}$ may define have various relative sizes with respect to each other. For example, in some configurations, a ratio of $W_{FS}/W_{FR}$ may be from about 1.2 to about 3.5, specifically reciting all 0.1 increments within the above-recited ranges and all ranges formed therein or thereby.

As shown in FIG. 11, the first nonwoven dead zone $NW_{DZ1}$ may define a width $W_{NWDZ1}$ in the cross direction CD, and the second nonwoven dead zone $NW_{DZ2}$ may define a width $W_{NWDZ2}$ in the cross direction CD, wherein $W_{NWDZ1}$ may be equal to or different than $W_{NWDZ2}$. In some configurations, the width $W_{NWDZ1}$ and/or the width $W_{NWDZ2}$ may be from about 1 mm to about 5 mm, specifically reciting all 1 mm increments within the above-recited ranges and all ranges formed therein or thereby. In some configurations, the width $W_{NWDZ1}$ and/or the width $W_{NWDZ2}$ may be from about 0 mm to about 15 mm, specifically reciting all 1 mm increments within the above-recited ranges and all ranges formed therein or thereby. The first film dead zone $F_{DZ1}$ may define a width $W_{FDZ1}$ in the cross direction CD, and second film dead zone $F_{DZ2}$ may define a width $W_{FDZ2}$ in the cross direction CD, wherein $W_{FDZ1}$ may be equal to or different than $W_{FDZ2}$. In some configurations, the width $W_{FDZ1}$ and/or the width $W_{FDZ2}$ may be from about 7 mm to about 12 mm, specifically reciting all 1 mm increments within the above-recited ranges and all ranges formed therein or thereby. In some configurations, the width $W_{FDZ1}$ and/or the width $W_{FDZ2}$ may be from about 6 mm to about 15 mm, specifically reciting all 1 mm increments within the above-recited ranges and all ranges formed therein or thereby. In addition, the widths of the nonwoven dead zones $W_{NWDZ1}$, $W_{NWDZ2}$ may be equal to or different from the widths of the film dead zones $W_{FDZ1}$, $W_{FDZ2}$. In some configurations, the combination of the first nonwoven dead zone $NW_{DZ1}$ and the first film dead zone $F_{DZ1}$ may define a first dead zone $D_{Z1}$ of the waist gasketing element 858, and the combination of the second nonwoven dead zone $NW_{DZ2}$ and the second film dead zone $F_{DZ2}$ may define a second dead zone $D_{Z2}$ of the waist gasketing element 858. Thus, the first dead zone $D_{Z1}$ may define a width $W_{DZ1}$ in the cross direction CD that is equal to the sum of the width $W_{NWDZ1}$ and the width $W_{FDZ1}$, and/or the second dead zone $D_{Z2}$ may define a width $W_{FDZ2}$ in the cross direction CD that is equal to the sum of the width $W_{NWDZ2}$ and the width $W_{FDZ2}$. It is also to be appreciated that the mechanical bonds 172, 272, 372, 472, 772 discussed herein may extend in the cross direction CD for distances that are less than, equal to, or larger than the width $W_{DZ1}$ and/or the width $W_{DZ2}$. In some configurations, the waist gasketing element 858 may not include the first nonwoven dead zone $NW_{DZ1}$ and/or the second nonwoven dead zone $NW_{DZ2}$. As such, the first film dead zone $F_{DZ1}$ may define the first dead zone $D_{Z1}$ of the waist gasketing element 858, and the second film dead zone $F_{DZ2}$ may define a second dead zone $D_{Z2}$ of the waist gasketing element 858. Thus, the width $W_{DZ1}$ may be equal to the width $W_{FDZ1}$, and/or the width $W_{DZ2}$ may be equal to the width $W_{FDZ2}$.

It is to be appreciated the waist gasketing element 858 may be configured such that the width $W_{DZ1}$ of the first dead zone $D_{Z1}$ may be equal to or different from the width $W_{DZ2}$ of the second zone $D_{Z2}$. In some configurations, the width $W_{DZ1}$ of the first dead zone $D_{Z1}$ width and the width $W_{DZ2}$ of the second dead zone $D_{Z2}$ may each be equal to, less than, or greater than a width of the adhesive-free zones of the waist gasketing element 858.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article, comprising:
    a front waist region, a back waist region, and a crotch region disposed between the front and back waist regions;
    a longitudinal axis and a lateral axis;
    a front waist edge, a back waist edge, a first side edge extending longitudinally and a second side edge extending longitudinally;
    a chassis comprising a topsheet, a backsheet, and an absorbent core disposed between the topsheet and the backsheet;
    a waist gasketing element comprising a proximal end edge, a distal end edge, and a first side edge and a second side edge, wherein the waist gasketing element is a laminate comprising a first nonwoven and an elastic film, the waist gasketing element further comprising a stretch zone positioned between a first film dead zone and a second film dead zone, the elastic film is configured to extend and contract in the stretch zone while remaining unstretched in the first and second film dead zones;
    a leg gasketing element comprising a proximal end edge, a distal end edge, a first side edge and a second side edge, and an elastic material; and
    wherein at least a portion of the waist gasketing element is adhesively attached to the chassis and wherein at least a portion of the waist gasketing element is mechanically attached to the chassis, wherein the waist gasketing element comprises an adhesive zone, a first adhesive-free zone, and a second adhesive-free zone.

2. The disposable absorbent article of claim 1, wherein the first adhesive-free zone is disposed at and adjacent to the first side edge of the waist gasketing element and the second adhesive-free zone is disposed at and adjacent to the second side edge of the waist gasketing element.

3. The disposable absorbent article of claim 2, wherein the waist gasketing element comprises a third adhesive-free zone disposed at and adjacent to the proximal end edge of the waist gasketing element at a central region of the waist gasketing element, such that the proximal end edge of the waist gasketing element at the central region is not attached to the chassis.

4. The disposable absorbent article of claim 2, wherein the waist gasketing element comprises a third adhesive-free zone disposed at and adjacent to the proximal end edge of the waist gasketing element at a central region of the waist gasketing element, and wherein the adhesive zone is disposed at and adjacent to the distal end edge of the waist gasketing element.

5. The disposable absorbent article of claim 1, wherein first and second mechanical bonds attach the waist gasketing element to the chassis.

6. The disposable absorbent article of claim 5, wherein the first and second mechanical bonds overlap the first and second adhesive-free zones, respectively.

7. The disposable absorbent article of claim 5, wherein the adhesive zone does not comprise the first and second mechanical bonds.

8. The disposable absorbent article of claim 5, wherein the first and second mechanical bonds extend through the waist gasketing element, the topsheet, and the backsheet.

9. The disposable absorbent article of claim 5, wherein the first and second mechanical bonds extend through the waist gasketing element, a leg gasketing element, the topsheet, and the backsheet.

10. The disposable absorbent article of claim 5, wherein the first and second mechanical bonds extend through the waist gasketing element, the topsheet, and the backsheet, and a landing zone.

11. The disposable absorbent article of claim 5, wherein the first and second mechanical bonds each comprise groupings of mechanical bonds.

12. The disposable absorbent article of claim 1, wherein the laminate further comprises a second nonwoven, and the elastic film is disposed between the first and second nonwovens, wherein the first nonwoven is ultrasonically bonded to the second nonwoven.

13. The disposable absorbent article of claim 12, wherein the first and second nonwovens are connected through the elastic film.

14. The disposable absorbent article of claim 1, wherein the laminate does not comprise adhesive.

15. The disposable absorbent article of claim 1, wherein the waist gasketing element is an extrusion bonded laminate.

16. The disposable absorbent article of claim 1, wherein the waist gasketing element is a laminate comprising a plurality of bond sites arranged in a pattern.

17. The disposable absorbent article of claim 16, wherein the pattern comprises a non-linear arrangement of adjacent bond sites.

18. The disposable absorbent article of claim 17, wherein the plurality of bond sites are arranged in a wavy pattern.

19. The disposable absorbent article of claim 18, wherein a wave of bonds in the wavy pattern defines a wave amplitude and wherein consecutive bonds in the machine direction are separated by a bond distance.

20. The disposable absorbent article of claim 19, wherein the wave amplitude is at least half of the bond distance.

21. The disposable absorbent article of claim 1, wherein the waist gasketing element is an adhesively bonded laminate.

22. A disposable absorbent article, comprising:
a front waist region, a back waist region, and a crotch region disposed between the front and back waist regions;
a longitudinal axis and a lateral axis;
a front waist edge, a back waist edge, a first side edge extending longitudinally and a second side edge extending longitudinally;
a chassis comprising a topsheet, a backsheet, and an absorbent core disposed between the topsheet and the backsheet;
a waist gasketing element comprising a proximal end edge, a distal end edge, and a first side edge and a second side edge, wherein the waist gasketing element is a laminate comprising a first nonwoven and an elastic film, the waist gasketing element further comprising a stretch zone positioned between a first film dead zone and a second film dead zone, the elastic film is configured to extend and contract in the stretch zone while remaining unstretched in the first and second film dead zones;
a leg gasketing element comprising a proximal end edge, a distal end edge, a first side edge and a second side edge, and an elastic material; and
wherein at least a portion of the waist gasketing element is adhesively attached to the chassis and wherein at least a portion of the waist gasketing element is mechanically attached to the leg gasketing element, wherein the waist gasketing element comprises an adhesive zone, a first adhesive-free zone, and a second adhesive-free zone.

23. The disposable absorbent article of claim 22, wherein at least a portion of the waist gasketing element is mechanically attached to the chassis.

24. The disposable absorbent article of claim 22, wherein at least a portion of the waist gasketing element is mechanically attached to the topsheet.

25. The disposable absorbent article of claim 24, wherein at least a portion of the waist gasketing element is mechanically attached to the backsheet.

26. The disposable absorbent article of claim 25, wherein at least a portion of the waist gasketing element is mechanically attached to the chassis.

27. The disposable absorbent article of claim 22, wherein the first adhesive-free zone is disposed at and adjacent to the first side edge of the waist gasketing element and the second adhesive-free zone is disposed at and adjacent to the second side edge of the waist gasketing element.

28. The disposable absorbent article of claim 27, wherein the waist gasketing element comprises a third adhesive-free zone disposed at and adjacent to the proximal end edge of the waist gasketing element at a central region of the waist gasketing element, such that the proximal end edge of the waist gasketing element at the central region is not attached to the chassis.

29. The disposable absorbent article of claim 27, wherein the waist gasketing element comprises a third adhesive-free zone disposed at and adjacent to the proximal end edge of the waist gasketing element at a central region of the waist gasketing element, and wherein the adhesive zone is disposed at and adjacent to the distal end edge of the waist gasketing element.

30. The disposable absorbent article of claim 22, wherein the waist gasketing element is a first waist gasketing element and a second waist gasketing element is disposed in the front waist region.

31. The disposable absorbent article of claim 30, wherein the second waist gasketing element comprises a third adhesive-free zone disposed at and adjacent to a proximal end edge of the second waist gasketing element at a central region of the second waist gasketing element, such that the proximal end edge of the second waist gasketing element at the central region is not attached to the chassis.

32. The disposable absorbent article of claim 30, wherein the first waist gasketing element comprises a third adhesive-free zone disposed at and adjacent to the proximal end edge of the first waist gasketing element at a central region of the first waist gasketing element, such that the proximal end edge of the first waist gasketing element at the central region is not attached to the chassis, and wherein a proximal end edge of the second waist gasketing element at a central region is attached to the chassis.

* * * * *